(12) United States Patent
Trier et al.

(10) Patent No.: US 10,653,884 B2
(45) Date of Patent: May 19, 2020

(54) DIGITAL CONTROL FOR PULSE GENERATORS

(71) Applicant: Nuvectra Corporation, Plano, TX (US)

(72) Inventors: Stephen C. Trier, Mayfield Heights, OH (US); Jeffrey A. Weisgarber, Jewett, OH (US); Richard J. Polefko, Parma, OH (US); David J. Howard, North Ridgeville, OH (US)

(73) Assignee: NUVECTRA CORPORATION, Plano, TX (US)

(*) Notice: Subject to any disclaimer, the term of this patent is extended or adjusted under 35 U.S.C. 154(b) by 21 days.

(21) Appl. No.: 15/726,458

(22) Filed: Oct. 6, 2017

(65) Prior Publication Data

US 2018/0104492 A1    Apr. 19, 2018

Related U.S. Application Data

(63) Continuation of application No. 14/041,082, filed on Sep. 30, 2013, now Pat. No. 9,782,587.

(60) Provisional application No. 61/708,211, filed on Oct. 1, 2012.

(51) Int. Cl.
*A61N 1/36* (2006.01)

(52) U.S. Cl.
CPC .......... *A61N 1/36125* (2013.01); *A61N 1/36* (2013.01); *A61N 1/36071* (2013.01); *A61N 1/36128* (2013.01)

(58) Field of Classification Search
None
See application file for complete search history.

(56) References Cited

U.S. PATENT DOCUMENTS

| | | |
|---|---|---|
| 4,898,173 A | 2/1990 | Daglow et al. |
| 5,417,714 A | 5/1995 | Levine et al. |
| 5,730,628 A | 3/1998 | Hawkins |
| 5,865,641 A | 2/1999 | Swart et al. |
| 6,029,090 A | 2/2000 | Herbst |
| 6,058,326 A | 5/2000 | Hess et al. |
| 6,120,467 A | 9/2000 | Scallhorn |
| 6,219,580 B1 | 4/2001 | Faltys et al. |
| 6,393,316 B1 | 5/2002 | Gillberg et al. |
| 6,421,566 B1* | 7/2002 | Holsheimer ......... A61N 1/3604 607/46 |

(Continued)

FOREIGN PATENT DOCUMENTS

| | | |
|---|---|---|
| DE | 10134277 A1 | 1/2003 |
| EP | 1995685 A2 | 11/2008 |

(Continued)

OTHER PUBLICATIONS

European Patent Office, European Office Action dated Feb. 7, 2018, Appln. No. 13186926.5. 5 pages.

(Continued)

*Primary Examiner* — Erica S Lee
(74) *Attorney, Agent, or Firm* — Haynes and Boone, LLP; Eric Li

(57) ABSTRACT

A controller for implementing a method, device and/or system for generating arbitrary waveforms of a desired shape that can be used for generating a stimulation pulse for medical purposes such as for spinal cord stimulation therapy, where such arbitrary waveforms can also be used for charge balancing purposes.

20 Claims, 30 Drawing Sheets

(56) References Cited

U.S. PATENT DOCUMENTS

| | | | |
|---|---|---|---|
| 6,505,077 B1 | 1/2003 | Kast et al. | |
| 6,516,227 B1* | 2/2003 | Meadows | A61N 1/0553 |
| | | | 607/117 |
| 6,622,048 B1 | 9/2003 | Mann et al. | |
| 6,625,488 B2 | 9/2003 | Poore et al. | |
| 6,659,968 B1 | 12/2003 | McClure | |
| 6,687,538 B1 | 2/2004 | Hrdlicka et al. | |
| 6,754,533 B1 | 6/2004 | Helfinstine et al. | |
| 6,892,098 B2 | 5/2005 | Ayal et al. | |
| 6,950,706 B2 | 9/2005 | Rodriguez et al. | |
| 7,065,412 B2 | 6/2006 | Swoyer et al. | |
| 7,177,691 B2 | 2/2007 | Meadows et al. | |
| 7,187,976 B2 | 3/2007 | Duncan et al. | |
| 7,236,822 B2 | 6/2007 | Dobak, III | |
| 7,263,400 B2 | 8/2007 | Helfinstine et al. | |
| 7,289,852 B2 | 10/2007 | Helfinstine et al. | |
| 7,483,748 B2 | 1/2009 | Torgerson et al. | |
| 7,493,159 B2 | 2/2009 | Hrdlicka et al. | |
| 7,526,338 B1 | 4/2009 | Gill et al. | |
| 7,551,964 B2 | 6/2009 | Dobak, III | |
| 7,647,111 B2 | 1/2010 | Ries et al. | |
| 7,680,540 B2 | 3/2010 | Jensen et al. | |
| 7,702,385 B2 | 4/2010 | Moffitt et al. | |
| 7,715,912 B2 | 5/2010 | Rezai | |
| 7,805,197 B2 | 9/2010 | Bradley | |
| 7,813,809 B2 | 10/2010 | Strother et al. | |
| 7,937,158 B2 | 5/2011 | Erickson et al. | |
| 8,024,035 B2 | 9/2011 | Dobak, III | |
| 8,180,445 B1* | 5/2012 | Moffitt | A61N 1/36146 |
| | | | 607/1 |
| 8,190,259 B1 | 5/2012 | Smith et al. | |
| 8,260,424 B2 | 9/2012 | Moffitt et al. | |
| 8,495,640 B2 | 7/2013 | Krauss | |
| 8,509,906 B2 | 8/2013 | Walker et al. | |
| 8,571,677 B2 | 10/2013 | Torgerson et al. | |
| 8,874,219 B2 | 10/2014 | Trier et al. | |
| 8,954,148 B2 | 2/2015 | Labbe et al. | |
| 8,996,115 B2 | 3/2015 | Trier et al. | |
| 8,996,117 B2 | 3/2015 | Trier et al. | |
| 2003/0125773 A1 | 7/2003 | Heathershaw et al. | |
| 2003/0171685 A1 | 9/2003 | Lesser et al. | |
| 2003/0204221 A1 | 10/2003 | Rodriguez et al. | |
| 2003/0204224 A1 | 10/2003 | Torgerson et al. | |
| 2003/0204225 A1 | 10/2003 | Heathershaw et al. | |
| 2004/0088025 A1* | 5/2004 | Gesotti | A61N 1/36003 |
| | | | 607/49 |
| 2004/0098067 A1 | 5/2004 | Ohta et al. | |
| 2005/0010625 A1 | 1/2005 | Andrews | |
| 2005/0027325 A1 | 2/2005 | Lahti et al. | |
| 2005/0179458 A1 | 8/2005 | Chen et al. | |
| 2006/0259098 A1 | 11/2006 | Erickson | |
| 2007/0078498 A1 | 4/2007 | Rezai et al. | |
| 2007/0200576 A1 | 8/2007 | Laurent et al. | |
| 2007/0213783 A1 | 9/2007 | Pless | |
| 2008/0140154 A1 | 6/2008 | Loeb et al. | |
| 2008/0177351 A1 | 7/2008 | Fang et al. | |
| 2009/0149917 A1 | 6/2009 | Whitehurst et al. | |
| 2009/0256583 A1 | 10/2009 | Chen et al. | |
| 2009/0265153 A1 | 10/2009 | Mazeau et al. | |
| 2010/0016850 A1 | 1/2010 | Ron Edoute et al. | |
| 2010/0063555 A1 | 3/2010 | Janzig et al. | |
| 2011/0029040 A1 | 2/2011 | Walker et al. | |
| 2011/0077717 A1 | 3/2011 | Poletto | |
| 2011/0160810 A1* | 6/2011 | Griffith | A61N 1/0531 |
| | | | 607/72 |
| 2011/0184496 A1 | 7/2011 | Kallmyer | |
| 2011/0208265 A1 | 8/2011 | Erickson et al. | |
| 2011/0270363 A1 | 11/2011 | Schramm et al. | |
| 2012/0071951 A1 | 3/2012 | Swanson | |
| 2012/0197330 A1 | 8/2012 | Crutchfield et al. | |
| 2012/0245664 A1 | 9/2012 | Smith et al. | |
| 2012/0265272 A1 | 10/2012 | Judkins | |
| 2013/0006330 A1 | 1/2013 | Wilder et al. | |
| 2013/0096641 A1 | 4/2013 | Strother et al. | |
| 2013/0197615 A1 | 8/2013 | Rundle et al. | |

FOREIGN PATENT DOCUMENTS

| | | |
|---|---|---|
| TW | 426868 B | 3/2001 |
| WO | WO 03090849 A1 | 11/2003 |

OTHER PUBLICATIONS

Extended European Search Report dated Aug. 1, 2014 for Application No. 13186926.5.

Gwilliam, et al., "A Charge-Balanced Pulse Generator for Nerve Stimulation Applications", Dept. of Bioengineering, University of Utah, http://www.sciencedirect.com (Sep. 12, 2007).

Ji-Jon Sit Sarpeshkar, R., "A Low-Power Blocking-Capacitor-Free Charge-Balanced Electrode-Stimulator Chip with Less than 6 Na Dc Error for 1-ma Full-Scale Stimulation", Mass. Inst. of Technol., Cambridge, pp. 172-183 (Sep. 2007).

Kataoka, et al., "Contact Properties of Ni Micro-Springs for MEMS Probe Card", pp. 231-235 (2004).

Pawel Hottowy, et al., "An Integrated Multichannel Waveform Generator for Large-Scale Spatio-Temporal Stimulation of Neural Tissue", Analog Integrated Circuits and Signal Processing, Klumer Academic Publishers, BO, vol. 55, No. 3, pp. 239-248 (Dec. 12, 2007).

* cited by examiner

| PH1 | WAVESHAPE | DELAY | AMP1 | AMP2 | AMP3 | ... | AMPN | ... |

| PH2 | WAVESHAPE | DELAY | AMP1 | AMP2 | AMP3 | ... | AMPN | ... |

⋮

| PHm | WAVESHAPE | DELAY | AMP1 | AMP2 | AMP3 | ... | AMPN | ... |

| SEQ | SPH | EPH |

Figure 5a

| PH1 | WAVESHAPE = HALFSINE | DELAY = 100us | AMP1 = +3000uA | AMP2 = -3000uA | AMP3 = 0uA | AMP4 = 0uA | ... | AMPN = 0uA |
|---|---|---|---|---|---|---|---|---|
| PH2 | WAVESHAPE = RECT | DELAY = 300us | AMP1 = -1000uA | AMP2 = +1000uA | AMP3 = 0uA | AMP4 = 0uA | ... | AMPN = 0uA |
| PH3 | WAVESHAPE = RECT | DELAY = 100us | AMP1 = 0uA | AMP2 = 0uA | AMP3 = +1000uA | AMP4 = -1000uA | ... | AMPN = 0uA |
| PH4 | WAVESHAPE = FALL EXP | DELAY = 100us | AMP1 = 0uA | AMP2 = 0uA | AMP3 = -1000uA | AMP4 = +1000uA | ... | AMPN = 0uA |
| PH5 | WAVESHAPE = RECT | DELAY = 100us | AMP1 = -2000uA | AMP2 = -1000uA | AMP3 = +1000uA | AMP4 = +2000uA | ... | AMPN = 0uA |
| PH6 | WAVESHAPE = RECT | DELAY = 400us | AMP1 = +1000uA | AMP2 = +500uA | AMP3 = -500uA | AMP4 = -1000uA | ... | AMPN = 0uA |
| PH7 | WAVESHAPE = NULL | DELAY = 0us | AMP1 = 0uA | AMP2 = 0uA | AMP3 = 0uA | AMP4 = 0uA | ... | AMPN = 0uA |
| ... | ... | ... | ... | ... | ... | ... | | ... |
| PHm | WAVESHAPE = NULL | DELAY = 0us | AMP1 = 0uA | AMP2 = 0uA | AMP3 = 0uA | AMP4 = 0uA | ... | AMPN = 0uA |

| SEQ | SPH = PH1 | EPH = PH6 |
|---|---|---|

Figure 5b

| PH1 | WAVESHAPE | REPETITIONS | DELAY | AMP1 | AMP2 | AMP3 | ... | AMPN |
|---|---|---|---|---|---|---|---|---|
| PH2 | WAVESHAPE | REPETITIONS | DELAY | AMP1 | AMP2 | AMP3 | ... | AMPN |
| ⋮ | | | | | | | | |
| PHm | WAVESHAPE | REPETITIONS | DELAY | AMP1 | AMP2 | AMP3 | ... | AMPN |

| SEQ | SPH | EPH |
|---|---|---|

Figure 9

DIGITAL CONTROL FOR PULSE GENERATORS

PRIORITY DATA

This application is a continuation of U.S. patent application Ser. No. 14/041,082, filed Sep. 30, 2013, now U.S. Pat. No. 9,782,587 which claims benefit of U.S. Provisional Application No. 61/708,211, filed Oct. 1, 2012, which are incorporated herein by reference in their entirety.

BACKGROUND

This application relates generally to a medical device, and more specifically, this application relates to a controller for an implantable medical device used, for example, for spinal cord stimulation therapy.

Programmable pulse generating systems are used to treat chronic pain by providing electrical stimulation pulses from an electrode array placed in or near a patient's spine. Such Spinal Cord Stimulation (SCS) is useful for reducing pain in certain populations of patients. SCS systems typically include one or more electrodes connected to an External Pulse Generator (EPG) or an Implanted Pulse Generator (IPG) via lead wires. In the case of an EPG, the lead wires must be connected to the EPG via an exit from the body. The pulse generator, whether implanted or external, generates electrical pulses that are typically delivered to the dorsal column fibers within the spinal cord through the electrodes which are implanted along or near the epidural space of the spinal cord. In a typical situation, the attached lead wires exit the spinal cord and are tunneled within the torso of the patient to a sub-cutaneous pocket where the IPG is implanted, or the wires exit the patient for connection to the EPG.

Neural stimulators for SCS to date have been limited to waveform shapes dictated by their circuitry. Most emit relatively simple rectangular or trapezoidal stimulation phases with exponential, clamped-exponential, or rectangular charge recovery phases. Implanted pulse generators to date have had a limited ability to generate complex trains of pulses. Often they are driven by simple timers which greatly limit the variety of pulse trains they can emit. Similar waveform limitations typically exist for stimulators used in other medical applications, such as cardiac implants, cochlear implants, etc. Furthermore, spinal cord stimulators have typically been limited to biphasic pulse output, where the first phase of the pulse provides the desired stimulation effect while the second phase of the pulse provides an equal but opposite amount of electrical charge to provide a net DC current of zero.

Nevertheless, it is desirable that other waveform shapes be available, as such shapes may be useful in controlling which nerve fibers respond to a stimulation pulse. For example, by allowing any type of waveform shape to be applied to any phase of a stimulation pulse, it may be possible to target specific types of nerve fibers for activation. It is also desirable to allow a stimulation pulse to have any number of phases, in particular more than the two phases typically used by neurostimulators, as this could allow pre-polarization of nerve tissue prior to the stimulation pulse. Finally, it is desirable to allow stimulation pulse phases to be interleaved in such a way that a second stimulation pulse is executed between the two phases of a first stimulation pulse, since this could allow one area of neural tissue to be pre-polarized prior to the stimulation of a second area of neural tissue. By using these new stimulation techniques, the goal is to allow greater control in selecting particular nerve fibers for activation, thus increasing the therapeutic benefit of neural stimulation while decreasing the side-effects.

Desired is a capability of producing complex waveforms of arbitrary shapes, whether or not they are inherently piecewise-linear, to allow greater flexibility in the number and sequence of pulse phases when constructing and executing stimulation waveforms. Also desired is the ability to adjust amplitudes and pulsewidths or to switch between multiple stimulation waveforms simply and efficiently, such as by using an efficient and accurate control method.

U.S. Pat. Nos. 7,483,748 and 6,950,706 disclose a way to assemble pulse trains from up-ramping, down-ramping and a constant voltage, driven from a system of counters and timers. But this approach lacks the ability to efficiently generate more sophisticated pulse trains such as pre-pulses, interleaved pulses, burst stimulation or n-lets. Providing a solution allowing these sophisticated pulse trains would be desirable.

Furthermore, capabilities for efficient, error-resistant updates to the stimulation program via double-buffering, storage of multiple programs simultaneously, and program interleaving to simulate, simultaneously, two different stimulation frequencies, is also desirable.

SUMMARY

Disclosed herein is a device/system capable of producing complex stimulation waveforms capable of having more than two phases per pulse. Such a device/system can have an arbitrary number of pulse phases and can execute the phases in any order. The device/system can also repeat one or more phases before proceeding to execute the next phase. Further disclosed herein is a device/system that can interleave phases from one stimulation pulse with those from another stimulation pulse.

Also disclosed herein is a device/system with a state machine architecture that allows a highly flexible means for generating stimulation pulse waveforms. This architecture uses a microcontroller running firmware and dedicated stimulation waveform generation circuitry to produce pulse trains heretofore unavailable in spinal cord stimulation systems.

Further disclosed herein is a device/system that can rescale portions of a stimulation waveform, including the pulse width, amplitude, waveshape, or frequency of one or more phases, without having to stop stimulation.

Also disclosed is a medical device for stimulating a stimulation region of a patient comprising: a waveform generation circuit for providing an output waveform by converting digital data into an analog signal for providing to the stimulation region of the patient; and a control device for controlling the waveform generation circuit. This control device is comprised of a state machine having a plurality of registers, the state machine being configured for directing the waveform generation circuit for generating the output waveform in a reproducible and repeatable manner.

Further provided is the above control device wherein the state machine includes a first plurality of phase registers such that each one of the first plurality of phase registers stores data for directing the waveform generation circuit for generating one of a plurality of different phase portions of an output pulse comprising the output waveform.

Also provided is the above control device having one or more additional registers for storing information such as an amplitude and/or a polarity for one phase portion of the output pulse; a delay value providing a delay time between the one phase portion and a following phase portion of the output waveform; a shape of one or more phases of output waveform; a first phase portion and a last phase portion of a portion of the output waveform; a shape of one or more portions of the waveform; the number of times that one or more phase portions should be repeated in series; a value indicating that the state machine should pause after executing a particular one of the plurality of phase portions; a value indicating whether a particular one of the phase portions should provide a synchronization signal.

Provided is a medical device for stimulating a stimulation region of a patient comprising: a waveform generation circuit for generating an output waveform for providing to the stimulation region of the patient; and a state machine comprising a first plurality of phase registers. The first plurality of first phase registers include: a plurality of first amplitude registers each configured for storing an amplitude of a respective phase portion of the output waveform, at least one first waveshape register configured for storing information about a shape of one or more phase portions of the output waveform, and at least one first control register configured for storing a control value utilized by the waveform generator for controlling a start, stop, and/or timing of the output waveform. The state machine also comprising a second plurality of phase registers including: a plurality of second amplitude registers each configured for storing an amplitude of a respective phase portion of the output waveform, at least one second waveshape register configured for storing information about a shape of one or more phase portions of the output waveform, and at least one second control register configured for storing a control value utilized by the waveform generator for controlling a start, stop, and/or timing of the output waveform. The device also includes a programmable controller for executing a program for controlling the operation of the state machine.

The programmable controller in the above device is configured for instructing the state machine for directing the waveform generation circuit for generating a first part of the output waveform based on the values stored in the first plurality of phase registers, and the programmable controller is configured for instructing the state machine for directing the waveform generation circuit for generating a second part of the output waveform based on the values stored in the second plurality of phase registers such that the first part of the output waveform transitions to the second part of the output waveform in a continuous manner.

Further provided is a method of controlling a medical device, comprising the steps of:

a controller issuing a first load command to load a first plurality of registers in a state machine;

loading each one of at least a first subset of the first plurality of registers in the state machine with a respective one or more first waveshape generation value(s) adapted for controlling the operation of a waveform generator;

the controller issuing a run command instructing the state machine to control the waveform generator to generate an output waveform based on the first waveshape generation values stored in the first subset of the first plurality of registers, wherein each one of the first waveshape generation values is utilized by the waveform generator for determining the magnitude, phase, and/or shape of a different portion of the output waveform.

Also provided is the above method further comprising the steps of:

the controller issuing a second load command to load a second plurality of registers in the state machine;

loading each one of at least a first subset of the second plurality of registers in the state machine with a respective one or more second waveshape generation value(s) adapted for controlling the operation of the waveform generator; and the controller issuing a transition command instructing the state machine to transition the waveform generator from generating the output waveform using the first waveshape generation values to generating the output waveform using the second waveshape generation values for changing the output waveform in a continuous manner without interruption.

Also provided is the above method further comprising the step of loading each one of a second subset of the first plurality of registers with a respective delay value, wherein each one of the delay values is utilized by the waveform generator for determining a delay between a different one and another of the different portions of the output waveform.

Further provided is the above method also comprising the step of loading one or more others of the first plurality of registers with a respective control value, wherein the control values are utilized by the waveform generator for controlling a start, stop, and/or timing of the output waveform.

Also provided is the above method further comprising the step of loading each one of a second subset of the second plurality of registers with a respective second delay value, wherein each one of the second delay values is utilized by the waveform generator for determining a delay between a different one and another of the different portions of the output waveform after issuance of the transition command.

Also provided are additional embodiments, some, but not all of which, are described hereinbelow in more detail.

BRIEF DESCRIPTION OF THE DRAWINGS

The features and advantages of the examples described herein will become apparent to those skilled in the art upon reading the following description, with reference to the accompanying drawings, in which:

FIG. 5a shows a simplified diagram of example phase registers provided in an example sequencer;

FIG. 5b shows example programming of registers of an example sequencer to produce the pulse trains shown in FIG. 4;

FIG. 9 is a diagram showing example phase registers of another

DETAILED DESCRIPTION OF THE EXAMPLE EMBODIMENTS

Figure 1:
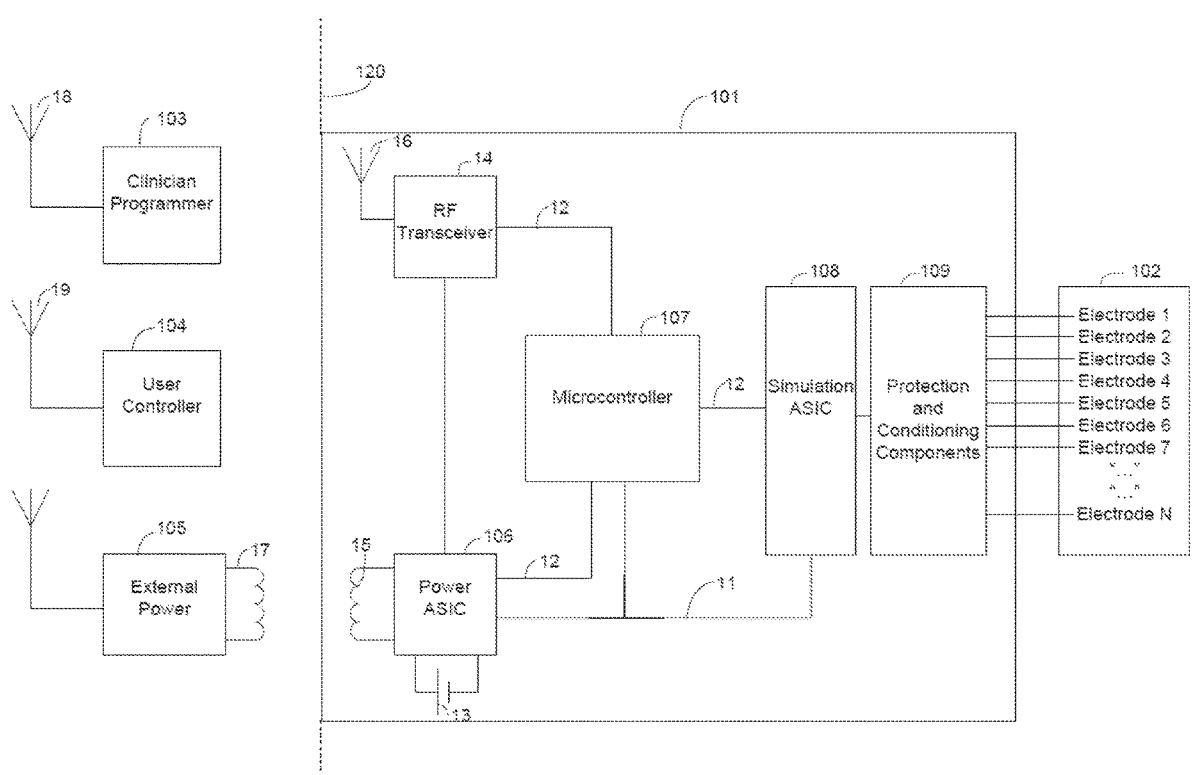
FIG. 1 is a block diagram showing an example embodiment of a pulse stimulation system.

Provided is a method and device, or system of devices cooperating with each other, for providing digital logic for a medical device, such as one that can provide a flexible and highly adaptable stimulation waveform, such as might be used for medical purposes such as spinal stimulation (such as for pain reduction, for example). This system includes a neurostimulation pulse generator that uses digital waveform synthesis techniques to generate stimulation pulses with programmable waveshapes. Such pulse generators are described, among others, in U.S. patent application Ser. Nos. 13/081,936; 13/081,896; and 13/082,097; all filed on Apr. 7, 2011, and incorporated herein by reference in their entirety. Thus, this disclosure describes examples of digital logic that can be used to control the waveform generators of the example devices described in those applications.

An example of a controller for controlling an implantable pulse generator (IPG) (such as described in the example patent applications listed above) is a sequencer (e.g., a state machine) comprised of circuit elements that allow a flexible method for programming a complex series of pulses for electrical stimulation. Fundamentally, this example solution divides the series of pulses into a sequence of phases and delays. One element of this design is a set of programmable registers that define each phase of the series of pulses. These registers define such things as the amplitude, polarity, pulse width, and waveshape of all active channels during each phase, among other parameters.

Another element of this example design is a state machine called the "sequencer", which uses information from the registers and from external control lines to construct the desired series of pulses in the IPG. Yet another element of this example design is a control interface that allows for precise control of the sequencer using a microcontroller that is running software programs stored in memory for implementing the desired functionality (throughout this document, the use of the term "microcontroller" means the hardware microcontroller and the software, memory and other support circuits for implementing the desired functionality). The control interface allows for precise timing of the phases while also allowing multiple methods for pulse control.

When these circuit elements are used together, they allow stimulation features heretofore unavailable in existing neurostimulation devices. Previously, stimulation pulses were limited to two phases: a programmable stimulation phase followed by a charge recovery phase that was often passive. The example designs and control methodology disclosed herein allow for more than two phases to be assigned to any pulse, and also allow for varied charge recovery phases that can be arbitrarily programmed. This means, for example, that stimulation features such as "pre-pulses," among others, can be implemented.

Pre-pulses can be implemented in neurostimulation therapies as sub-activation threshold currents that are applied prior to the stimulation phase of the pulse. The purpose of adding a pre-pulse is to pre-polarize the tissue prior to the stimulation phase, providing some control over which nerve fibers are activated during the stimulation phase of the pulse. This is useful because nerve tissue, in particular the spinal cord and the dorsal roots, typically consists of several types of nerve fibers, with each type of fiber having a different threshold of activation. When stimulating the spinal cord, it is desired to activate certain types of nerves (e.g., sensory nerves) while avoiding the activation of other types of nerves (e.g., motor nerves). By using pre-pulses, it may be possible to polarize the nerve tissue in such a way that one type of nerve (e.g., sensory nerves) is activated while other types of nerves (e.g., motor nerves) are not activated.

Another feature built into this design structure is that the sequencer can allow any phase in the stimulation waveform to be repeated as desired. This means that a stimulation phase could be repeated multiple times, which allows stimulation waveforms known as "burst stimulation" or "n-lets" to be implemented. Using burst or n-let stimulation can be used to achieve different physiological effects than other stimulation waveforms, so this feature can prove useful for certain neurostimulation applications, and for future therapies not yet envisioned.

Yet another stimulation feature of the disclosed design is that it can provide interleaved pulses. In this feature, the stimulation phase of one pulse would be executed at one tissue area, followed by the stimulation phase of a second pulse impacting a different tissue area. By executing the second stimulation phase prior to recovering the charge from the first stimulation phase, it is possible to polarize one area of the tissue prior to stimulating another area of tissue. The charge recovery phases could then be executed after the second stimulation phase is completed.

To execute the example stimulation capabilities described above, one example approach presented in this disclosure involves the execution of a stimulation waveform as a pre-programmed sequence of phases and delays which make up a "pulse train". The pulse train may consist of a single traditional two-phase stimulation pulse (e.g., a single stimulation phase followed by a charge balancing phase) or may consist of many phases and delays (e.g., multiple stimulation pulses or a single stimulation pulse with more than two phases). A set of registers dedicated to controlling the sequence of phases and delays is provided, such as determining the phase at which the pulse train starts and the phase after which the pulse train ends. In addition, each phase can have its own set of registers. These phase-specific registers select the waveshape to be used during that phase, determine the amplitude, polarity, and pulse width of all active channels during that phase, control the delay time that is implemented following the completion of the phase, determine what type of charge balancing to use during a delay (if any), and control the number of times the phase and delay are to be repeated before moving on to the next phase. In this structure, each pulse train can begin or end at any phase in the register map.

The state machine, or sequencer, as disclosed herein is responsible for stepping through the phase registers as desired. The core of the sequencer is relatively straightforward—it receives an indication to start the pulse train from an external source, then proceeds to step through each phase and delay as programmed until executing the final phase or delay in the sequence. At this point, the sequencer can stop, providing a single run through the pulse train, or it can go back to the beginning (or some other point) of the sequence and start the sequence again, or provide another different sequence, all while providing a continuous mode of operation.

A control interface for connecting to a control device such as a microcontroller can be provided that comprises a set of inputs and outputs that can be used to operate the sequencer in various modes. For example, as described above, the core of the sequencer can use one input to provide a starting signal, and a second input to determine whether the sequencer functions in single-run or continuous operation. These two inputs, along with the phase registers described above, provide a minimum functionality to perform pre-pulses, bursts, or n-lets. Another input that can be added to the sequencer is an indicator to stop the sequencer, so that stimulation may be stopped in the middle of a pulse train, such as due to some sort of error detected by the system. Yet another input would be an indicator to change the set of registers from which the pulse train is executed, allowing quick transitions between one pulse train and another different pulse train.

In addition, there are several example outputs that could be provided by the sequencer to enhance its controllability. First, an output may be added to indicate to the rest of the system (medical device) that a stimulus pulse is being actively generated. Second, a programmable synchronization output may be included, allowing the sequencer to drive this output to certain states at desired phases in the pulse train. Third, a programmable pause feature may be included, where the sequencer pauses after executing a certain phase, then waits for indication from an external source to resume the pulse train from the point at which it paused.

An example state machine could be implemented in software executing on a processor that is coupled to a stimulation waveform generator, or, as is the primary focus here, using dedicated hardware separate from (or even instead of) a programmable processor. In one example implementation, hardware is incorporated in an application-specific integrated circuit (ASIC) that also includes a waveform generator, amplitude multipliers, and various other components provided for supporting the stimulation function.

An example hardware implementation uses a microcontroller (processor) to provide a means to configure the state machine prior to the sequencing of stimulation output. An interface between the microcontroller and the state machine (such as through a communication bus or dedicated control lines, for example) permits the division of responsibility between the state machine hardware and the microcontroller (executing software or firmware) to take many forms along a spectrum, from detailed interaction between the microcontroller and the state machine within the pulse train, to "set-and-forget" operation in which the microcontroller starts the state machine running and need not interact with the state machine again until the pulse train parameters are changed, or the pulse train is to be stopped.

The example design is highly configurable, allowing the same hardware design/device to potentially be used for very different pulse trains developed for particular therapies.

The design and implementation of the state machine in hardware allows for a range of control interaction between the state machine and a microcontroller, ranging from minimal interaction to highly interactive. Minimal interaction brings numerous advantages that come along with a lower performance/cost processor that may also save on power usage and generate less heat. Highly interactive control allows for a greater level of flexibility in operation of the state machine and coordination with other activities of the neurostimulator. Intermediate levels of interaction, of course, offer tradeoffs between these extremes.

Embodiments of a "Waveform Generator for Neural Stimulation" such as can use such a sequencer as disclosed herein are found in U.S. patent application Ser. Nos. 13/081,936; 13/081,896; and 13/082,097; that were filed on Apr. 7, 2011, and are incorporated herein by reference.

Components of a Stimulation System

A complete implanted neurostimulator system is comprised of an implanted pulse generator (IPG) that connects to one end (a connector) of an implanted lead. The other end of the implanted lead includes one or multiple electrode surfaces through which electrical current is applied to the desired tissue. The implanted lead incorporates electrical conductors that provide a path for that current to travel to the tissue from the IPG. An IPG may connect to one or more implanted leads, typically two or three leads, although more can be accommodated. Power is provided to the IPG, as desired, by an external charger for charging the IPG power supply. The IPG may incorporate power-storage components such as a battery or a capacitor, or some other energy storage device so that it may be powered independently of the charger for a period of time, typically from several days to a month or more depending on the power requirements of the therapeutic electrical stimulation delivered by the IPG. The system also includes one or more patient programmers, which are intended for use by the patient in whom the IPG is implanted. The patient may adjust the parameters of the stimulation, such as by selecting a stimulation program; changing its amplitude, frequency, and other parameters; and by turning stimulation on and off. Another component of the system is a clinician programmer, which is used by a medical clinician to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

FIG. 1 shows a block diagram of a specific example neurostimulator system where most of the components for generating the stimulation waveform are implanted in a patient for providing medical therapy by utilizing an implantable PG (IPG) 101 that could utilize the disclosed features. This system is comprised of the IPG 101 that includes a stimulation ASIC 108 and protection components 109. The IPG 101 is further comprised of a microcontroller 107 for controlling the functions of the IPG via the control bus 12, and a power ASIC 106 for powering the components via a power bus 11. Because this implantable system avoids the need for any components or wires that exit the body of the patient 120, the IPG 101 includes an RF transceiver (transmitter/receiver) 14 with an antenna 16 for allowing the IPG to communicate with devices external to the patient's body, such as a clinician programmer 103 and user controller(s) 104, which also have antennas 18 and 19, respectively, to communicate with the transceiver 14 via a wireless protocol.

Furthermore, the IPG also includes an embedded power supply including a power ASIC 106 for conditioning the device power, a rechargeable battery 13, and an inductive secondary coil 15 (or some other means) for receiving power from an external source outside the body of the patient 120. A corresponding external power supply 105 would typically require a corresponding primary charging coil 17 to complete the power connection to the embedded power supply to charge the battery 13. The IPG 101 is connected to one or more electrode arrays 102 including a plurality of electrodes via a header (not shown) connected via feedthroughs (not shown) to the protection components 109. The IPG 101 is provided in a hermetically sealed case made of, or coated by, human implantable compatible materials, and requiring only that the contacts attached to the lead body of the electrode array(s) be electrically connectable to the IPG through the header. The electrode leads and electrodes themselves, along with portions of the header that are exposed to the patient, must all be made of, or coated by, materials that are compatible with implantation in the human body.

Figure 2:
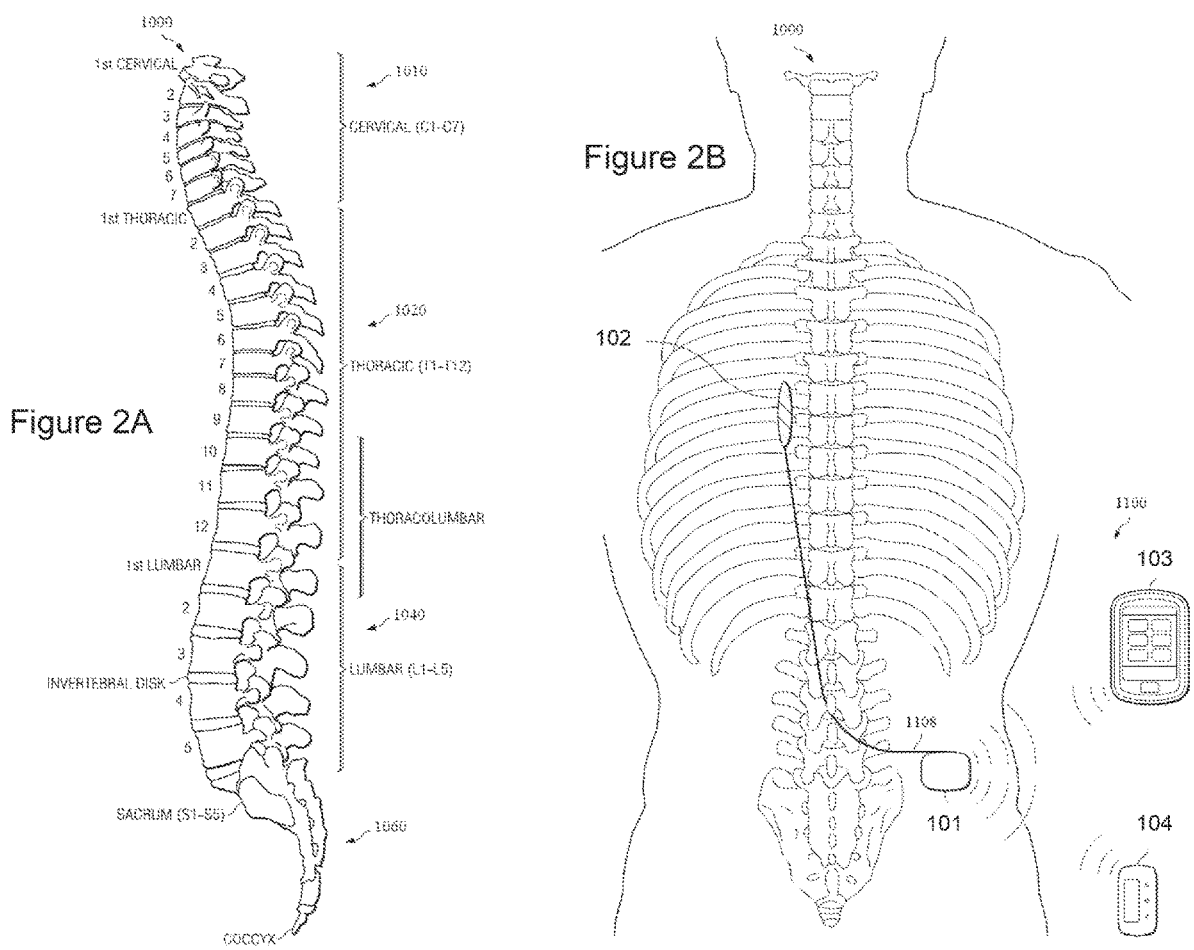
FIG. 2A is a generic diagram of the spine of a human being.
FIG. 2B is a schematic diagram showing a pulse stimulation system such as the system of FIG. 1 implanted in a patient.

FIG. 2A is a side view of a spine 1000 standing alone, and FIG. 2B is a posterior view of the spine 1000 in a patient. FIG. 2B shows an example electrical stimulator treatment system 1100 (such as the system shown in FIG. 1, for example) disposed to treat a spinal region for treating a symptom, such as chronic pain, of the patient. The system includes an implantable pulse generator (IPG) 1101 that delivers electrical stimulation therapy to the patient, and dual patient controllers shown and described as a user controller 1104 and a clinician programmer 1103.

Referring again to FIGS. 2A and 2B, the spine 1000 includes a cervical region 1010, a thoracic region 1020, a lumbar region 1040, and a sacrococcygeal region 1060. The cervical region 1010 includes the top seven vertebrae, which may be designated with C1-C7. The thoracic region 1020 includes the next twelve vertebrae below the cervical region 1010, which may be designated with T1-T12. The lumbar region 1040 includes the final five "true" vertebrae, which may be designated with L1-L5. The sacrococcygeal region 1060 includes nine fused vertebrae that make up the sacrum and the coccyx. The fused vertebrae of the sacrum may be designated with S1-S5.

Neural tissue (not illustrated for the sake of simplicity) branches off from the spinal cord through spaces between the vertebrae. The neural tissue, along with the cord itself, can be individually and selectively stimulated in accordance with various aspects of the present disclosure. For example, referring to FIG. 2B, the IPG 101 is implanted inside the body. A conductive lead 1108 is electrically coupled to the circuitry inside the IPG 101. The conductive lead 1108 may be removably coupled to the IPG 101 through a connector, for example. A distal end of the conductive lead 1108 is attached to one or more electrodes 102. In the example shown, the electrodes 102 are implanted adjacent to a desired nerve tissue in the thoracic region of the spinal chord 1000. The distal end of the lead 1108 with its accompanying electrodes may be positioned beneath the dura mater such as by using well-established and known techniques in the art.

The electrodes 102 deliver current drawn from the IPG 101, thereby generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, bladder control, weight control, or regulation of heart beats.

It is understood that the IPG 101, the lead 1108, and the electrodes 102 may be implanted completely inside the body, may be positioned completely outside the body, or may have only one or more components implanted within the body while other components remain outside the body. When implanted inside the body, the implant location may be adjusted (e.g., anywhere along the spine 1000) to deliver the intended therapeutic effects of spinal cord electrical stimulation in a desired region of the spine. The IPG 101 in this example system is a fully implantable, battery-powered neurostimulation device for providing electrical stimulation to a body region of a patient. In the example shown in FIG. 2B, the IPG 101 is configured to provide neural stimulation to the spine. However, in other embodiments, IPG 101 may be a different type of pulse generator, including, for example, a pacemaker, a defibrillator, a temporary trial stimulator, or any other type of medical device. In this example, the IPG 101 is structurally configured and arranged for wireless programming and control through the skin of the patient. Accordingly, it includes a transmitter and receiver capable of communicating with external programming and control devices, such as the user controller 104, and the clinician controller/programmer 103. Not shown in FIG. 2B is an external charger or power source for wirelessly recharging a rechargeable power source, such as a battery in the IPG 101. The IPG 101 is configured to be wirelessly recharged through the patient's skin when the primary coil of the external charger is externally placed in the proximity of the IPG 101.

The user controller 104 can provide more limited functionality relative to the functionality of the clinician controller/programmer 103 for controlling and programming the IPG 101. The clinician programmer 103 performs all the functions of the user controller 104, but also includes more advanced features and functionality for controlling and programming the IPG 101 to be used by a professional, and is a device typically maintained in a health care provider's possession and can be used to program the IPG 101 during office visits. For example, the clinician programmer can define the available stimulation programs for the device by enabling and disabling particular stimulation programs, can define the actual stimulation programs by creating defined relationships between pulses, and perform other functions.

Such a system is disclosed in U.S. patent application Ser. Nos. 13/170,775 and 13/170,558, incorporated herein by reference. In addition, more complex controllers (not shown) can be provided to the patient in order to provide more functionality than can be provided in the user controller 104.

Example embodiments can be equally applicable to an external pulse generator (EPG). An EPG is intended to be worn externally to the body. It connects to one end of one or more percutaneous, or skin-penetrating, leads. The other end of the percutaneous lead is implanted within the body and incorporates multiple electrode surfaces analogous in function and use to those of an implanted lead. A complete system incorporating an EPG may include a patient programmer, a clinician programmer, or an external charger, as shown in FIGS. 1 and 2A and 2B and described above.

Figure 3:
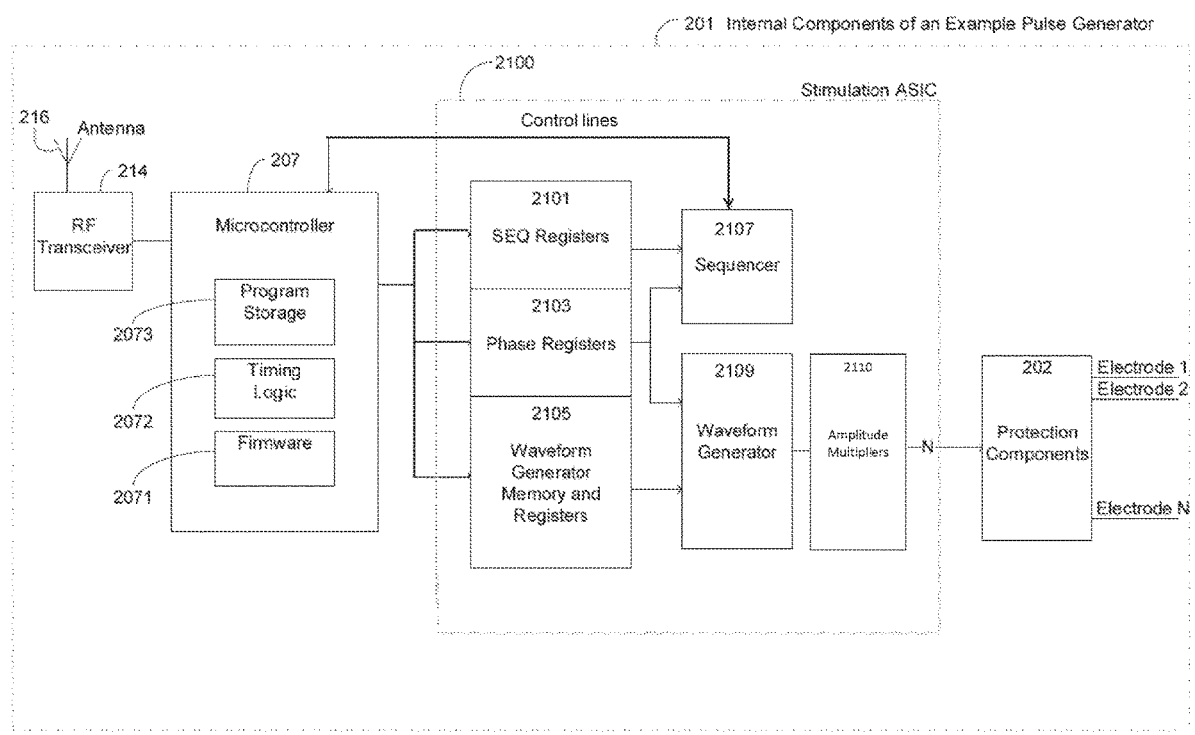
FIG. 3 is a block diagram showing the components of an example embodiment of a pulse generator using a sequencer controller as disclosed herein.

A block diagram of the internal components of an example pulse generator (PG) 201 is shown in FIG. 3, which may be utilized to provide the IPG 101 described above, or that may be an EPG as also described above. Power-related components, such as those to receive and/or store power, are also utilized by the PG 201 but are omitted from the figure for simplicity.

The Microcontroller 207 can be implemented using a microcontroller typical of those used in the industry. In the example device, a Texas Instruments MSP430F2618 can be used, but many other types could be used instead. The Microcontroller 207 includes Firmware 2071, which is a series of computer instructions executed by the microcontroller 207 that operate the PG 201, and it also includes Timing Logic 2072, which may provide some level of timing control for control of the stimulation. The Timing Logic 2072 may be implemented in hardware, Firmware 2071, Program storage 2073, or a combination of them. Another key component of the Microcontroller 201 is Program Storage 2073, which may be implemented in RAM, EEROM, or other memory and which holds the programs to be run by the PG 201. The Microcontroller 207 communicates and controls the RF Transceiver 214 and Stimulation ASIC 2100 via various signals, including serial interfaces to read and write the registers and memory on the RF Transceiver 214 and the Stimulation ASIC 2100.

The RF Transceiver 214 permits the PG 201 to communicate with an external user controller, clinician programmer, or external power source. A variety of suitable transceivers exist that can be utilized for the RF Transceiver 214. In an example device, a Zarlink ZL70102 and its supporting components are used for the transceiver. The Antenna 216 is used by the Transceiver 214 to transmit and receive at radio frequencies.

The Stimulation ASIC 2100 is an example of an Application-Specific Integrated Circuit (ASIC) incorporating digital and analog circuitry for the purpose of generating electrical stimulation. In the example device, the Stimulation ASIC 2100 is a custom-designed integrated circuit that is described in more detail herein. The Stimulation ASIC 2100 includes several types of registers that can be written to and read by the Microcontroller 207. There are Sequence (SEQ) registers 2101 that contain information about the starting and stopping points for the various pulse trains stored in Stimulation ASIC 2100. There are Phase registers 2103 that contain specific information about each phase in each pulse train stored in the Stimulation ASIC 2100. There are Waveform Generator memory and registers 2105 that store waveshape information that can be used in any phase executed by the pulse trains stored in Stimulation ASIC 2100. Additional components could be included in the Stimulation ASIC 2100 for some embodiments to provide additional functionality.

The three key components of the Stimulation ASIC 2100 for generating stimulation output are the Sequencer 2107, the Waveform Generator 2109, and the Amplitude Multipliers 2110. The Sequencer 2107 is a state machine, such as described above, that is controlled by the data in the SEQ registers 2101 and Phase registers 2103 and also controlled via control lines from the Microcontroller 207. The Sequencer 2107 uses the data stored in the SEQ and Phase registers 2101, 2103 and inputs from Microcontroller 207 to control the Waveform Generator 2109 and to execute the desired pulse train.

The output of the Waveform Generator 2109 is used as a reference waveshape for the Amplitude Multipliers 2110. The Amplitude Multipliers 2110 scale the amplitude and polarity of the reference waveshape generated by the Waveform Generator 2109 for each channel that is active during each phase in the pulse train being executed. An example of similar architecture comprising the Waveform Generator and Amplitude Multipliers is described in U.S. patent application Ser. Nos. 13/081,936; 13/081,896; and 13/082,097; all filed on Apr. 7, 2011, and incorporated herein by reference in their entirety. These architectures can also utilize a sequencer design such as described herein.

The outputs from the Amplitude Multipliers 2110 pass through a set of Protection Components 202, which provide such functions as protecting tissue from harm by blocking DC current flow and protecting the PG from harm by limiting and/or dissipating the energy received from various external electromagnetic sources, such as defibrillation, electrocautery, electrostatic discharge (ESD) and magnetic resonance imaging (MRI), among others.

After passing through the Protection Components 202, the outputs are coupled to a set of electrodes, via the implanted and percutaneous leads as described above, but not specifically shown in this figure. These electrodes are surgically placed near appropriate tissue, in such a way that the pulse train generated by the PG will stimulate the tissue and create the desired therapeutic benefit.

Pulse Train and Basic State Machine

Neurostimulators function by delivering a series of electrical pulses to nervous tissues of the body. By doing so, the stimulators can change the function of the tissue and related bodily systems in various therapeutic ways, such as relieving pain or controlling tremors or seizures, among others. The series of electrical pulses consist of several elements that are combined to create a "pulse train".

In an example embodiment described herein, each pulse within the pulse train is divided into multiple portions, each called a "phase". Each phase has associated with it a waveshape having, at all points within it, a relative magnitude of 0 to a maximum value, inclusive. That maximum value is 255 in the example implementation. This value is proportionally converted into a current (or voltage) in the actual pulse by the output of the PG to provide to the tissue via the electrodes. Each phase also has associated with it a delay that is executed immediately after the phase, and during this delay no stimulation current (or voltage) is generated. In this example embodiment, the delay can be programmed to zero if desired so that a next phase can be executed immediately after the previous phase ends.

The waveform generation circuitry in the example neurostimulator can be used to multiply the waveshape of each phase by a different positive or negative scaling factor for each output channel. A different set of scaling factors can be used for every phase in a pulse train. Thus, complex pulse trains comprising of a series of phases, with positive and negative outputs on various combinations of channels, may be created.

Figure 4:
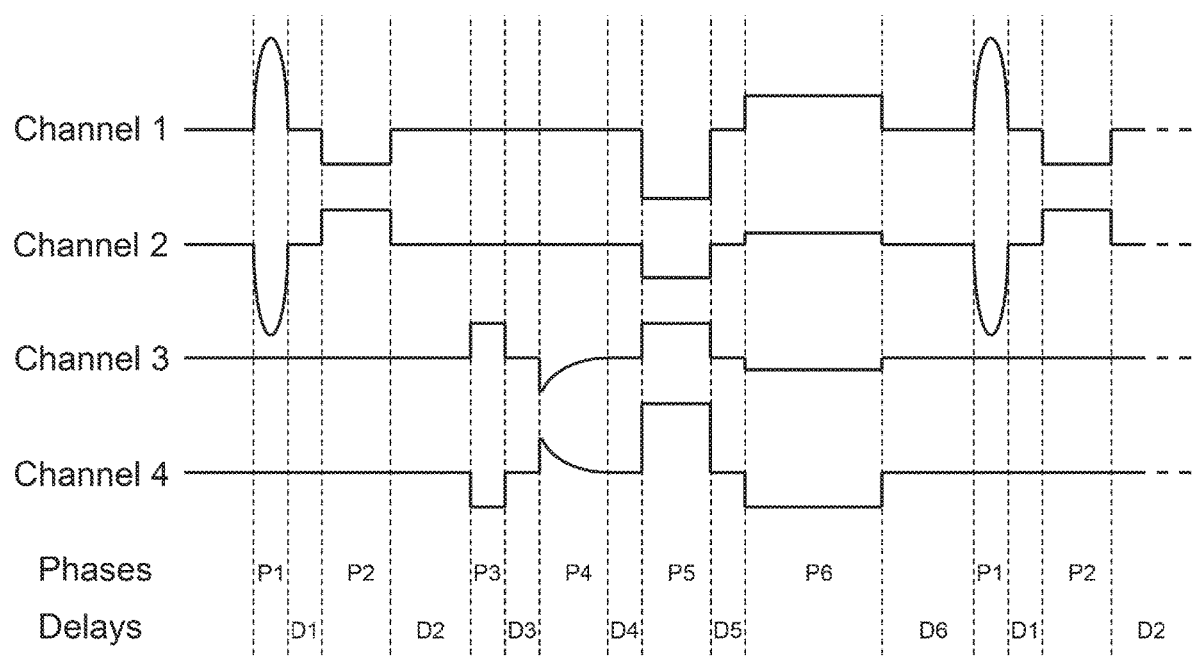
FIG. 4 is an example plot of a repeating pulse train that can be generated using an example sequencer as disclosed herein.

FIG. 4 shows an example of a repeating pulse train composed of multiple phases P1-P6 and delays 01-06, for each channel. Four stimulation channels are shown for illustration, though a typical stimulator may comprise any number of channels, up to 16, 32, or more. In phase P1, channels 1 and 2 are active, generating a half-sine stimulation waveshape followed by delay 01, during which all channels are off. Then in phase P2, channels 1 and 2 are active again, this time with opposite polarities as in phase P1 to balance the charge delivered during phase P1. Also, the stimulation amplitude in phase P2 is lower and the stimulation duration longer, and phase P2 also uses a rectangular waveshape. Alternating phases on the same channels, as is illustrated here, is often used to reduce the net DC current delivered to tissue to near zero, providing substantial charge balancing, which reduces the risk of electrode corrosion and tissue damage. Phase P2 is followed by delay D2.

The pulse train continues with phase P3, delay D3, phase P4, and delay D4. Phase P3 is rectangular once again, but phase P4 shows an exponential waveshape. In phases P3 and P4, channels 3 and 4 are active, while channels 1 and 2 are off.

The pulse train completes with phase P5, delay D5, phase P6, and delay D6, in which rectangular stimulation is used for each phase with all four channels active. While phases P5 and P6 each have a rectangular waveshape, the output is scaled differently in amplitude and polarity for each of the channels.

One complete cycle of the pulse train is executed from the start of phase P1 to the end of delay D6, after which the pulse train is restarted for another run. For this example, each run is comprised of the same phases in the same order. The pulse train may be run once or as many times as needed to provide the desired therapeutic effect. Of course, pulse trains could also be created comprised of any these, or other, phases, provided in a different order, or using other combinations of phases and delays.

In the example embodiment using the state machine, pulse trains such as these are created by the state machine using data stored in sets of phase registers. In this example, these registers are implemented in digital hardware in Stimulation ASIC 2100 of FIG. 3. FIG. 5a shows a simplified view of the phase registers. There are m sets of phase registers, numbered PH1 through PHm. Each set describes one phase and contains multiple registers that are configured by the microcontroller and read by the sequencer and waveform generator. The WAVESHAPE register or registers in each set control the stimulation waveshape for the phase, which may include the pulse width, the overall shape of the desired stimulation output waveform, and other parameters.

For example, the WAVESHAPE register or registers might permit choosing between a waveshape with a directly-generated shape or a waveform created by passively discharging a capacitor. The latter can be useful for obtaining a net DC current of zero, which is desirable for reasons mentioned previously. The DELAY register configures the duration of the delay after the stimulation phase and holds the number of clock cycles the state machine should delay before starting the next phase. The AMP1 through AMPN registers contain the amplitude and polarity for channels 1 through N for a system providing N channels. An amplitude of zero is permitted and indicates that the corresponding channel should emit no output during that phase. The AMP1 through AMPN registers may also hold additional configuration information for each channel during that phase. Finally, each set of phase registers may include additional registers to control additional features of the neurostimulator.

In addition, FIG. 5a shows a SEQ, or sequence, register, which holds an SPH value and an EPH value. This register identifies which phase register sets comprise the pulse train, with SPH holding the number of the first phase register bank in the pulse train and EPH holding the number of the last phase register bank in the pulse train.

FIG. 5b shows an example of how the phase and SEQ registers could be programmed to produce the pulse trains shown in FIG. 4. For the first phase P1, a half-sine waveshape is selected with the amplitudes for channels 1 and 2 set to +3000 uA and −3000 uA, respectively, with all other channels turned off and with a delay D1 of 100 us after the first phase is executed. For the second phase P2, a rectangular waveshape is selected with the amplitudes for channels 1 and 2 set to −1000 uA and +1000 uA, respectively, with all other channels turned off and with a delay D2 of 300 us after the second phase is executed. The third through sixth phases P3-P6 and corresponding delays D3-D6 are programmed in a similar manner, and all remaining phase registers PH7 through PHm are not programmed (i.e., are set to null or zero) in this example. The SEQ registers are programmed such that the starting phase of the stimulation program is PH1 while last phase is PH6.

Figure 6:
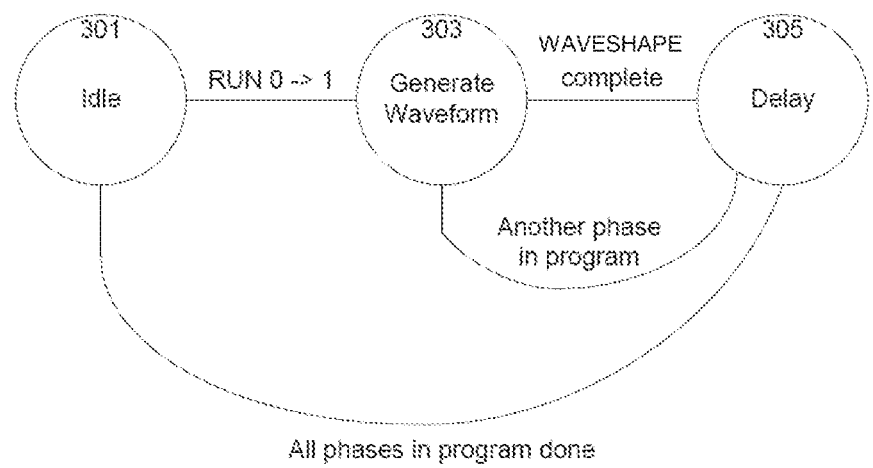
FIG. 6 shows an example state diagram of a simplified example state machine (sequencer)

FIG. 6 shows a state diagram of an example simplified state machine (sequencer) that uses the phase register sets and sequence registers as described above as well as a control line named RUN which is controlled by the microcontroller as an input to the state machine. The state machine starts in the Idle state 301, in which all channels' outputs are off. When the state machine detects the RUN signal transitioning from 0 to 1, it enters the generate waveform state 303 for the first phase register set in the pulse train, as configured in the SPH register. In this generate waveform state 303, the waveform generator (for example, as described above) is signaled to generate a waveshape in accordance with the values stored in the phase register set. The sequencer waits until the waveshape is complete, then it enters the Delay state 305. In this delay state 305, it counts clock cycles until the number configured in the phase's DELAY register have elapsed. After the duration configured in DELAY has elapsed, if the current phase is equal to EPH, the state machine reenters the Idle state 301. Otherwise, it increments the current phase and reenters the Generate Waveform state 303, generating the waveshape for the new current phase, and so forth.

Thus, the state machine operating as shown in FIG. 6 generates phases and delays in accordance with the parameters configured in each phase register set numbered from SPH to EPH as shown in FIG. 5a, in sequence, to execute one iteration of the pulse train. The mechanisms used to repeat a pulse train, as shown in FIG. 4, will be discussed later in this document.

Interleaved Pulses and Pre-Pulses

The simplified register set of FIG. 5a and state machine of FIG. 6 can be used to create other useful forms of a stimulation pulse train, examples of which are described below.

Figure 7A:
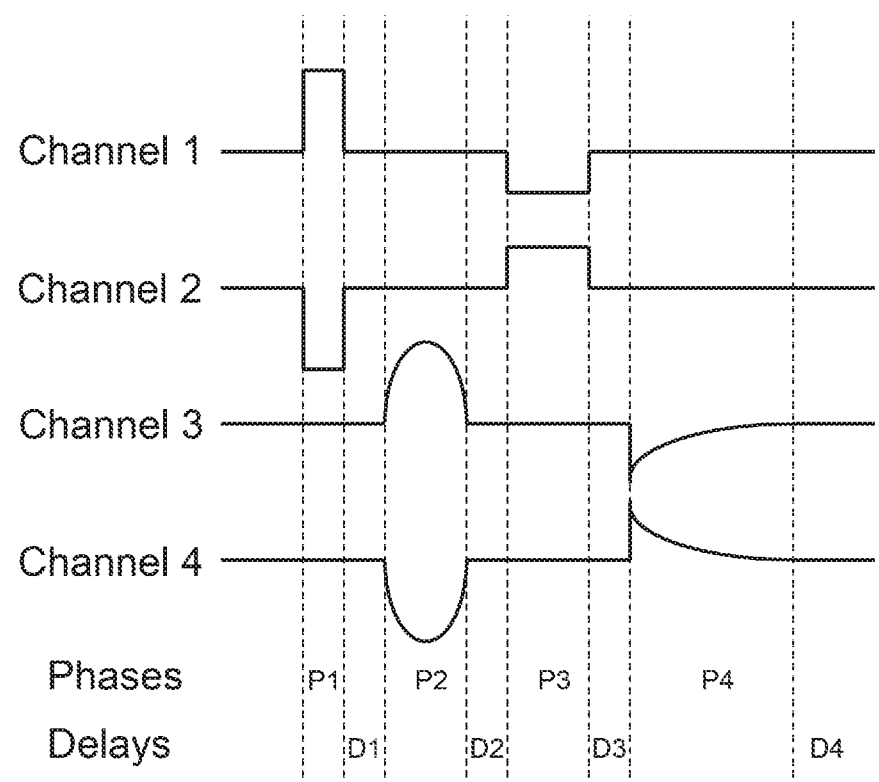
FIGS. 7a and 7b show plots of example interleaved pulses that can be produced by an example sequencer.
Figure 7B:
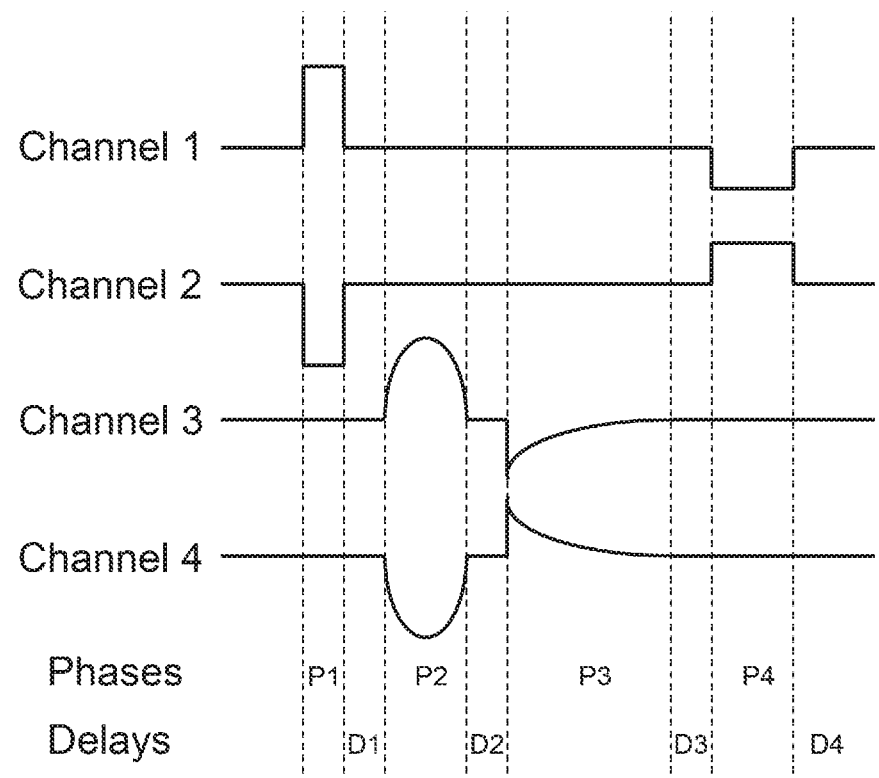

By polarizing one region of tissue before delivering stimulation to another region of tissue, interleaved pulses may be useful in enhancing the positive effects and/or reducing the negative effects of stimulation by targeting the activation of specific nerve fibers and/or by blocking neural activity in certain regions. FIGS. 7a and 7b show examples of interleaved pulses. In FIG. 7a, an initial phase of stimulation is applied to channels 1 and 2 (phase P1) to pre-polarize the tissue near the distal electrodes connected to channels 1 and 2. Typically, after executing delay D1, a charge-balancing phase would be applied to channels 1 and 2. However, as shown in FIG. 7a, delay D2 is followed by the initial phase of stimulation on channels 3 and 4 (phase P2). The charge-balancing phases follow delay D2, first on channels 1 and 2 (phase P3) and later on channels 3 and 4 (phase P4), reducing the net DC current on all four channels to near 0. FIG. 7b shows similar interleaving, with the exception that the charge-balancing phase for channels 3 and 4 (phase P3) is executed prior to the charge-balancing phase for channels 1 and 2 (phase P4). The pulse trains of both FIGS. 7a and 7b can be represented with the phase register sets of FIG. 5a by configuring the phase register sets for the interleaved pulse phases, in sequence, then using the state machine of FIG. 6 to generate the phases in order.

Figure 8:
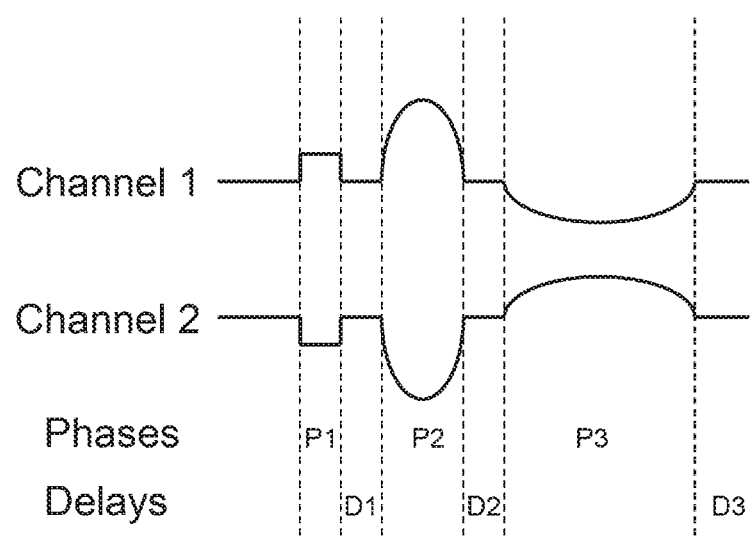
FIG. 8 shows a plot of an example of a pulse using a pre-pulse phase.

Another way to control the response of tissue to stimulation is to use more than two phases per pulse. Phases that precede the main stimulation phase are known as "pre-pulses", and have the benefit of pre-polarizing the neural tissue prior to the stimulation phases that follow. FIG. 8 shows an example of a pulse composed of a pre-pulse (phase P1) preceding two other phases (phases P2 and P3). As with interleaved pulses, pulses having one or more pre-pulse phases can be expressed with the phase register sets of FIG. 5a and the state machine of FIG. 6, by loading the phase register sets with the appropriate values to describe each phase of the pulse, then configuring and running the state machine to generate those phases in sequence.

Repeating Individual Phases

Pulses that are comprised of multiple identical smaller phases in place of a single larger phase can be used. This type of stimulation can be used to provide "burst" or "n-let" stimulation, in which the stimulation effect from using multiple smaller phases has a beneficial effect when compared to a single larger phase. A limitation of the phase register sets and state machine as described above is that each of those identical smaller phases must consume one phase register set. As an example solution shown in FIG. 9, each phase register set can include a REPETITIONS register, which represents a count of the number of times the phase should be repeated before proceeding to the next phase. In an example embodiment, the REPETITIONS register is four bits wide and represents 1 to 16 repetitions of the phase.

Figure 10:
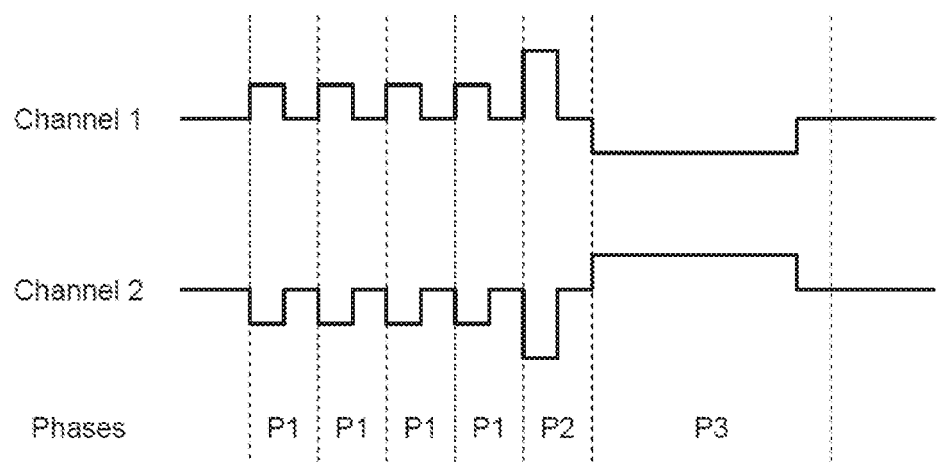
FIG. 10 shows an plot of an example sequencer using a REPETITIONS register.

FIG. 10 shows an example of using the REPETITIONS register to emit four pre-pulses before two other phases of a pulse. The phase P1 has its REPETITIONS register set to repeat the phase four times, while phases P2 and P3 have their REPETITIONS registers set for only a single instance of the phase. Without the REPETITIONS register, this pulse would require six phase register sets. With the REPETITIONS register, it can be stored in only three.

Figure 11:
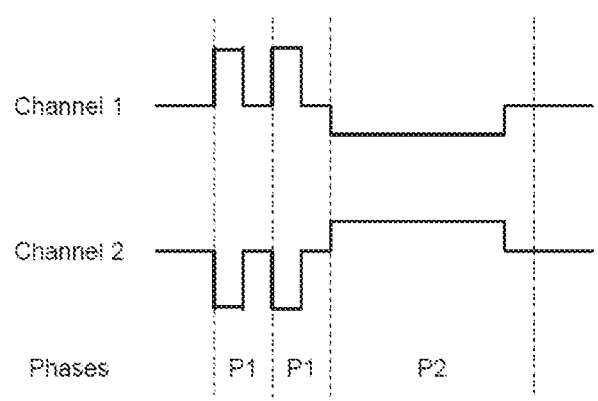
FIG. 11 shows a plot demonstrating the use of the REPETITIONS register.

Similarly, FIG. 11 demonstrates using the REPETITIONS register to emit a brief stimulation phase twice before proceeding with the second phase. Here, the REPETITIONS register permits the pulse to be represented by two phase register sets instead of three.

Sequencer Start

As described earlier, the example sequencer state machine requires a start signal to transition from the Idle state to the Generate Waveform state. In an example embodiment shown in FIG. 6, this start signal is provided by a RUN input to the state machine. When the state machine is in the Idle state 301 and the RUN signal transitions from 0 to 1, the state machine switches to the Generate Waveform state 303. Any time after the state machine goes into Generate Waveform state 303, the RUN signal may be set to 0. RUN is edge-sensitive, so if the state machine enters the Idle state 301 before RUN is 0, it remains in the Idle 301 until it sees a transition of RUN from 0 to 1.

As an aside, there are multiple conventions for representing logical values in electrical circuits, such as low-true and high-true, as well as a variety of voltages and currents, both positive and negative, used to represent logic states. Because the described example is independent of the logic convention used, this disclosure will use "0" and "1" to represent the two Boolean logic states. These states may be represented by any electrical convention, or by different conventions on different signals. Furthermore, substituting "1" for "0" and "0" for "1", in other words logical inversion, may be done for any of the signals described, without changing the nature of the example or its operation.

The RUN signal provides one way by which an example pulse train may be repeated at a desired frequency. The frequency for the pulse train repetition must be chosen so that it is low enough that the pulse train can complete one full cycle before the next cycle begins. In other words, the period needed to achieve the desired repetition frequency of the pulse train must be greater than or equal to the sum of the pulse widths for all phases and delays that comprise the pulse train. To achieve the desired repetition frequency of the pulse train, the microcontroller's Timing Logic must emit a rising edge on RUN at the desired frequency. With each rising edge on RUN, the sequencer leaves the Idle state, runs through the selected phase register sets, and enters the Idle state again. It remains in Idle until the next rising edge of RUN.

Figure 12:
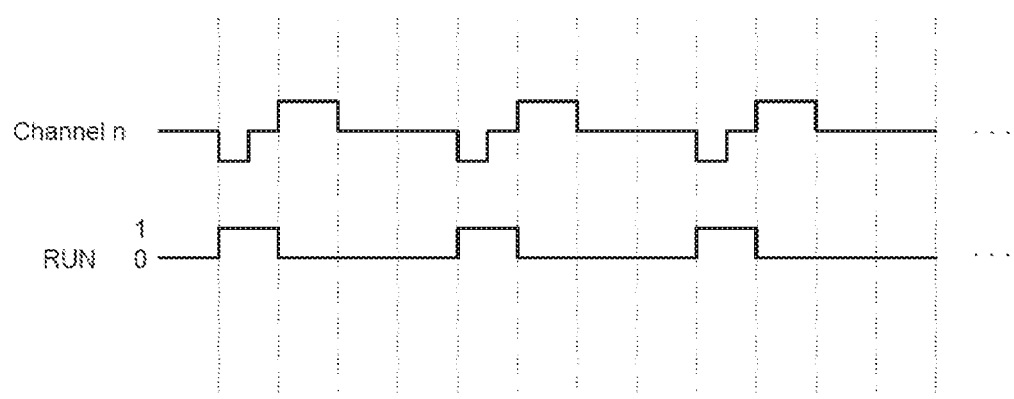
in FIG. 12 is a timing diagram illustrating the use of a RUN signal.

The timing diagram in FIG. 12 illustrates this use of the RUN signal. The RUN signal and one stimulation channel are shown, though the pulse train might involve any number of channels and phases. As indicated, each transition of RUN from 0 to 1 causes the sequencer to iterate through the pulse train from the first to last phase, and then transition to the Idle state to await the next 0 to 1 transition on RUN. The timing of the transition from 1 to 0 does not affect the pulse train output.

Continuous Operation

Pulsing RUN permits the microcontroller's Timing Logic to have direct control over the pulse train's frequency, but it has the drawback that the microcontroller must be sufficiently active during stimulation to generate repeated RUN pulses. Many microcontrollers have a variety of low-power modes that partially shut down sections of the controller, and it may be possible to have lower total system power consumption by having the sequencer state machine repeat the pulse train at the proper frequency without repeated pulses of RUN from the microcontroller, thus permitting the Timing Logic and Firmware to enter a lower-power mode of operation. Furthermore, pulsing RUN may cause the Timing Logic to consume excessive microcontroller resources, such as processor cycles, when running pulse trains at high frequencies.

To meet these needs with an example embodiment, an additional control signal, called CONT in this example, can be added to the sequencer state machine to allow the sequencer to operate continuously without intervention from the microcontroller. When the CONT signal is 1, the sequencer transitions not to the Idle state after the last phase of the pulse train, but instead to the Generate Waveform state for the first phase of the pulse train. It then repeats the phases of the pulse train in sequence. If CONT is 0 when the last phase of the pulse train completes, the sequencer transitions to Idle, as before. Therefore, setting CONT to 1 enables continuous generation of a pulse train, and setting CONT to 0 causes the pulse train to stop at that end of the pulse train's final phase. Keeping CONT at 0 while pulsing RUN permits pulse train repetition to be controlled by the microcontroller's Timing Logic, as described above, thus allowing two different modes for controlling the frequency at which the pulse train is repeated.

Figure 13:
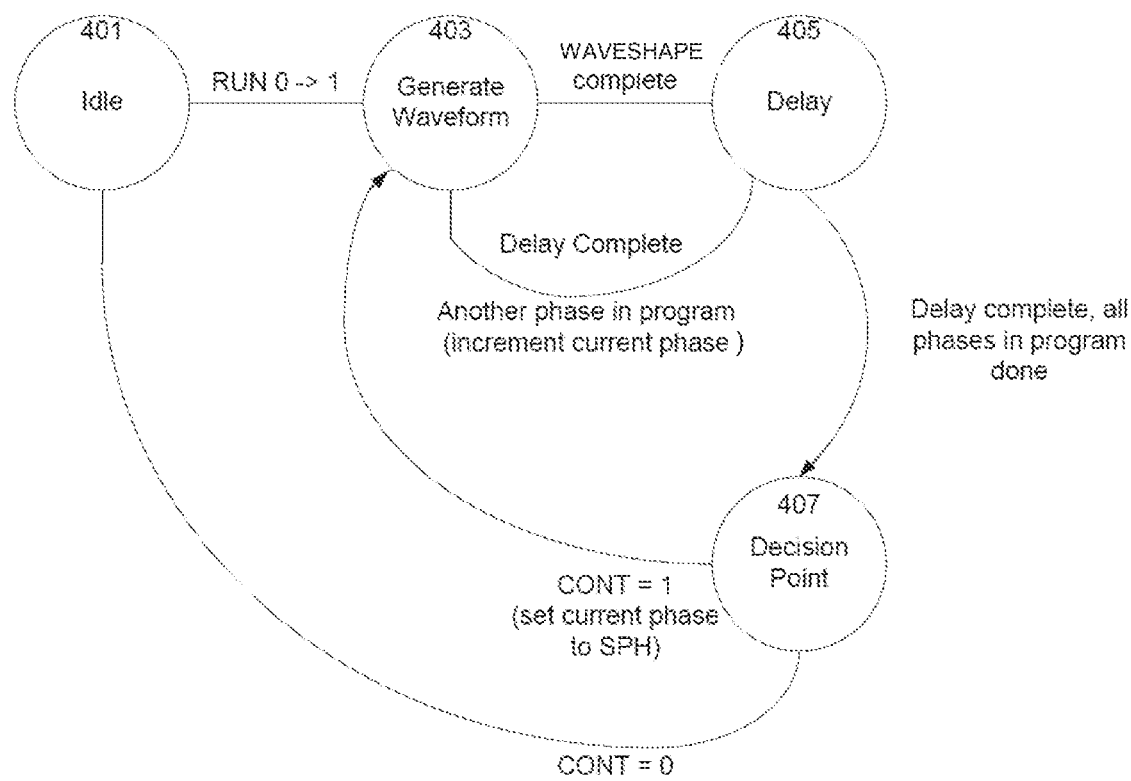
FIG. 13 shows a state diagram of an example sequencer that has both RUN and CONT inputs.

FIG. 13 shows a state diagram of an example sequencer state machine that has both RUN and CONT inputs. The state transitions are basically the same as in FIG. 6 (with an idle state 401, a generate waveform state 403, and a delay state 405), except that the transition out of the Delay state 405 occurs when all phases in the pulse train are complete, and it now goes to a decision point 407. If at the decision point CONT=1, the transition goes to Generate Waveform and the current phase becomes the value of SPH, while if CONT=0, the transition goes to Idle.

Figure 14:
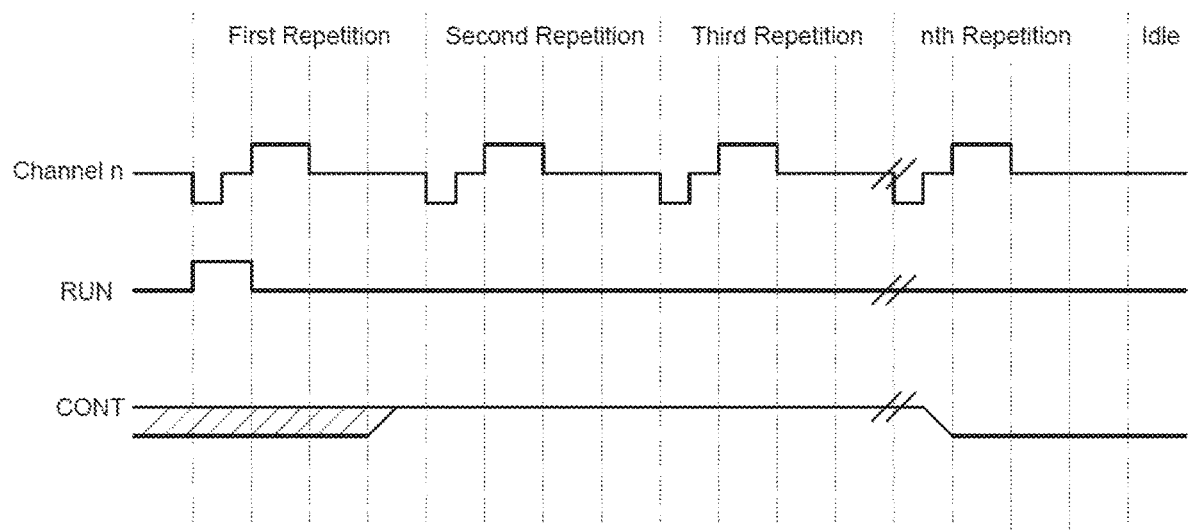
FIG. 14 shows a plot of control inputs that illustrates use of the CONT input to run a pulse train continuously.

FIG. 14 illustrates use of the CONT input to run a pulse train continuously. The pulse train is started by RUN going from 0 to 1. Sometime before or during the first cycle through the pulse train, the CONT signal goes to 1. At the end of the first run of the pulse train, the sequencer detects that CONT is 1 and repeats the pulse train. This continues until a repetition of the pulse train during which CONT goes to 0. When that repetition of the pulse train completes by executing its final phase, the sequencer detects that CONT is 0 and goes to the Idle state rather than repeating the pulse train.

When using CONT to run a pulse train continuously, the period and hence the frequency of the program is established by the sum of all pulse widths and delays in the pulse train. The frequency of the pulse train can be controlled in two ways. First, adjusting the length of one or more delays in the pulse train will change the frequency. Second, the pulse train may include a phase that has all channel amplitudes set to zero. The pulse width and/or delay of such a phase may be adjusted to control the pulse train's frequency.

Stopping the Program Early

In devices such as neurostimulators, there are often many fault detection methods and fail-safe mechanisms to protect the patient from harmful stimulation. In order to add a fail-safe mechanism to the sequencer state machine, a control signal called STOP can be added as an input to the sequencer. In this example, the STOP signal permits the microcontroller to end a program early if a fault is detected. When STOP is 1, the sequencer finishes the current phase, including the delay, then transitions to the Idle state. When STOP is 0, the sequencer operates normally. Because the current phase finishes, it is possible for the microcontroller to calculate precisely how much charge was dispensed on each channel, which may be important for ensuring net zero DC current.

Pause as an Alternative to Delays

It is sometimes desirable to have the microcontroller's Timing Logic control the duration of one or more of the delays in a pulse train. For example, the delay may be variable and calculated with a feedback algorithm running in real time. As another example, it may be desirable in some circumstances to have the Timing Logic directly control the duration of every delay in a pulse train. To permit direct control such as this, each phase register may include a PAUSE bit to indicate that the sequencer state machine should pause after executing that particular phase. In addition, the sequencer state machine may incorporate a decision point when leaving the Generate Waveform state.

Figure 15:
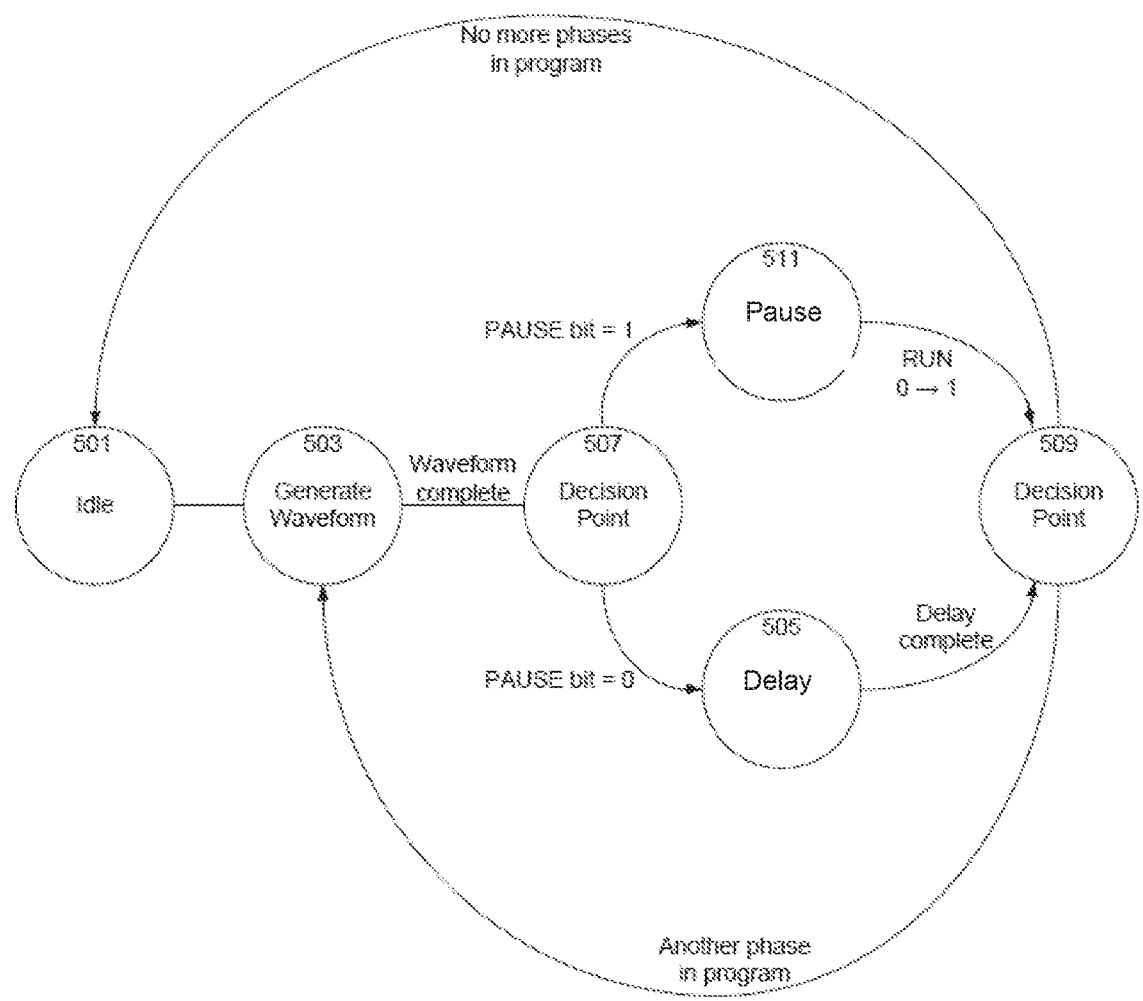
FIG. 15 shows a state diagram of an example sequencer incorporating a pause state.

FIG. 15 shows a state diagram of an example sequencer state machine (having an idle state 501, generate waveform state 503, and delay state 505) modified to incorporate the Pause state 511. At decision point 507, if the PAUSE bit for the phase is 0, the state machine enters the Delay state 505 and waits for the time specified by the DELAY register, as described previously. However, if the PAUSE bit is 1, the state machine enters the Pause state 511. It remains in Pause until a 0 to 1 transition on the RUN signal at decision point 509. When such a transition is seen, the state machine transitions to the Generate Waveform state 503 if there is another phase in the pulse train, or to the Idle state 501 if there are no more phases in the pulse train. This example is further enhanced with the addition of a control signal, labeled PAUSE, that can be connected between the sequencer state machine and the microcontroller to allow the sequencer to indicate to the microcontroller when the Pause state 511 has been entered. The PAUSE handshaking signal assists in synchronizing the sequencer and the microcontroller's Timing Logic. The PAUSE signal is an output from the sequencer that can be set to 1 when the sequencer is in the Pause state 511 and 0 otherwise, for example.

Figure 16:
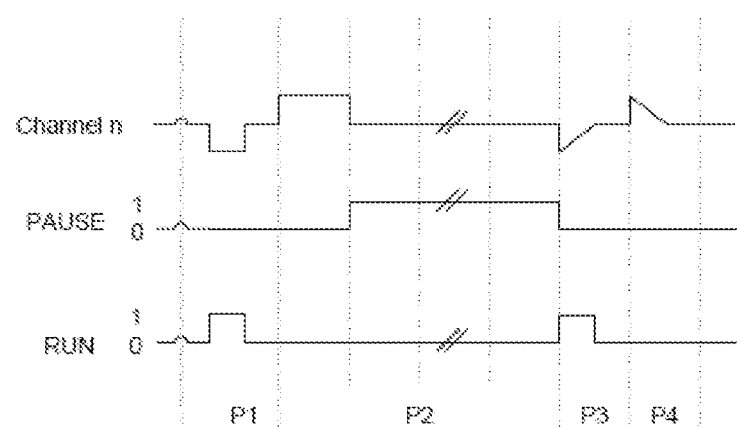
FIG. 16 shows a plot of control inputs illustrating use of a pause state.

FIG. 16 illustrates such a pause feature in operation. A four-phase pulse train (phases P1 through P4) has the PAUSE bit set in phase P2. As a result, the sequencer enters the Pause state instead of the Delay state in the latter portion of phase P2. The Pause state continues until the Timing Logic provides a 0 to 1 transition on the RUN signal, after which the Sequencer enters the Generate Waveform state for phase P3, and the pulse train continues to completion.

Other Synchronization Features

It is advantageous to consider providing additional control signals that would assist in synchronizing the sequencer state machine to the microcontroller's Timing Logic in more advanced embodiments of the sequencer. For example, it would be useful for the microcontroller to be able to verify whether the sequencer is actively generating a pulse train or whether it is idle. For this example, it would be useful to have an additional control signal, labeled PROG, that would indicate the state of the sequencer's activity. For example, the PROG signal could be set to 0 when the sequencer is in the Idle state and 1 otherwise. In other words, PROG is 1 whenever a pulse train is actively running and 0 when it is not. PROG is useful to the microcontroller as an acknowledgement for the RUN and STOP signals and to signal normal completion of a pulse train. It may also be used to synchronize the sequencer with other subsystems within the pulse generator, such as power supplies or sensor circuitry, among other possibilities.

To synchronize to one or more phases within a pulse train, it may be advantageous to include an additional feature that allows a control line to be set during specific phases in the pulse train. For example, it is possible to include a bit in each phase register set, called SYNC, that may be set by the firmware. In addition, the sequencer state machine could include an output called SYNC. At the start of each phase, the sequencer's SYNC output can be set to the value of the SYNC bit for that phase. Thus, synchronization with a particular phase can be done by setting the SYNC bit to 1 for that phase and 0 for every other phase in the pulse train, or vice versa. Synchronization with every phase in a pulse train can be done by programming SYNC to alternating values in each phase, using both the 0-to-1 and 1-to-0 transitions to mark the start of each phase.

Figure 17:
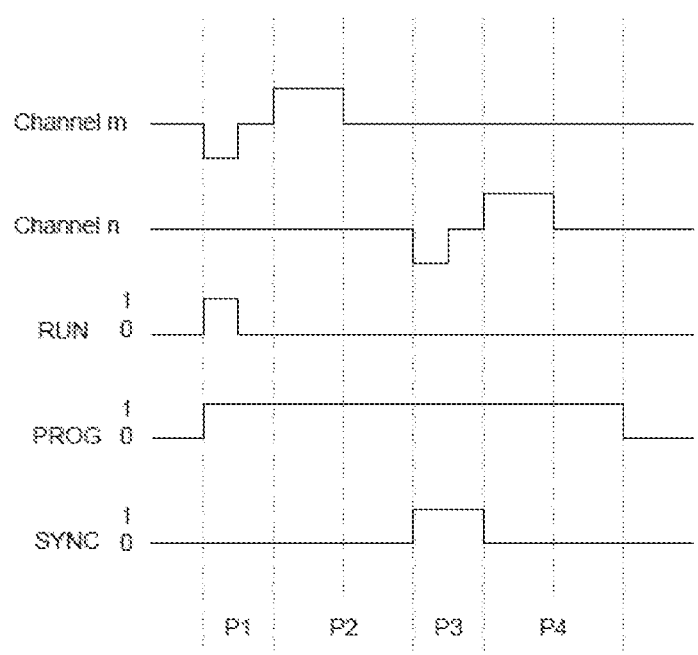
FIG. 17 shows a plot of control inputs illustrating operation of PROG and SYNC features.

The operation of the PROG and SYNC features described above is illustrated in FIG. 17. The pulse train is comprised of four phases, P1 through P4. In this example, the SYNC bit of each phase is 0, except for phase P3. When the RUN signal goes from 0 to 1, the sequencer begins phase P1 and sets the PROG output high. The pulse train runs through P1 and P2 with the SYNC signal equal to the SYNC bit value of 0 for those phases, but when it reaches P3, the sequencer sets SYNC to 1. When P4 begins, with its SYNC bit set to 0, the SYNC signal goes back to zero. After the last phase in the pulse train, P4, completes, the PROG output goes to 0 to indicate that the pulse train is complete and the sequencer is back into the Idle state. Thus, the microcontroller or other circuitry can obtain useful synchronization information by monitoring the PROG and/or SYNC signals.

Program Selection

It is desirable in some embodiments to be able to change stimulation parameters without disruption to the stimulation activity. In other words, it should be possible to change multiple parameters of one or more phases, then put all of those changes into effect simultaneously and without first stopping the pulse train's repetition. One solution to this problem is double-buffering, in which the sequencer and waveform generator run a pulse train from one set of phase registers while the firmware updates a second set. When the firmware is done updating the second set of phase registers, the microcontroller's Timing Logic instructs the sequencer to switch to the second set without disruption of the stimulation. If further changes are needed, the firmware may then update the first set of phase registers, which are no longer being used to generate the stimulation.

To permit this double-buffering approach, an alternative embodiment can be provided in which more than one SEQ register set is included, as opposed to the structure described earlier in which only one SEQ register set was shown. In this example, two SEQ register sets, named SEQ0 and SEQ1, are used. Both SEQ0 and SEQ1 hold an SPH and an EPH value. In this example, the sequencer state machine also has a SEL input that is controlled by the microcontroller. If the SEL input is 0 at the start of a pulse train cycle, the sequencer will use the SPH and EPH values in SEQ0 to generate the pulse train. Similarly, the sequencer will use the SPH and EPH values in SEQ1 if the SEL input is 1 at the start of a pulse train cycle. By setting the SEL input to the sequencer to 0 or 1, the microcontroller can select which phase registers are used by the sequencer to generate the pulse train. This also allows the sequencer to generate pulse trains from one set of phase registers while the microcontroller is updating a different set of phase registers. Once the microcontroller has completed updating the second set of phase registers, it can force the sequencer to switch to the second set of phase registers at the start of the next pulse train cycle by changing the state of the SEL input to the sequencer.

Two SEQ register sets and a SEL signal with two states is the minimum for this example. It can be seen how to generalize the structure to add more SEQ register sets and a corresponding number of states on the SEL signal. It is possible to have dedicated phase register structures with built-in buffering that do not require SEQ register sets. In addition, it is obvious that additional layers of buffering may offer additional benefits that are not described in this example.

A Comprehensive Example Embodiment

Now that simplified versions of the features of the device have been explained, a more comprehensive example embodiment can be discussed. It must be noted that while the structure described here will include all of the features discussed above, the structure allows both simple and complex operation and interaction between the microcontroller and Stimulation ASIC to provide many options for the generation of stimulation output.

Structure of the Phase Registers

Figure 18:
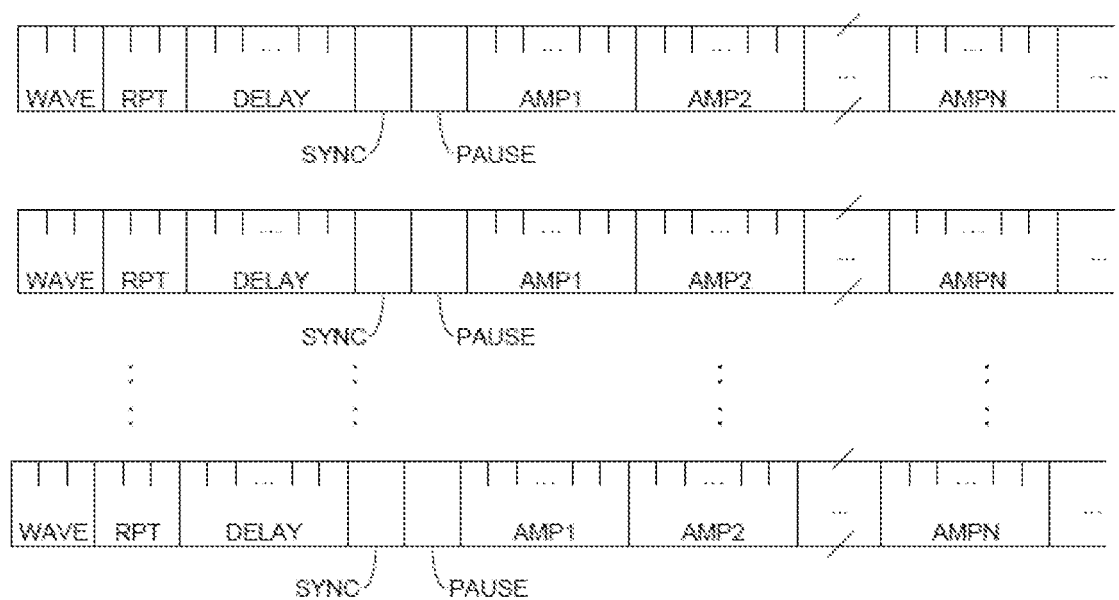
FIG. 18 is a diagram showing elements of phase registers for an example embodiment of the sequencer.

FIG. 18 shows the key elements of the phase registers in this example embodiment. Multiple banks of phase registers, numbered from 1 to m, are provided. In this example embodiment, m is 24, but other values can be used as desired. Each bank of registers represents one phase of a pulse train and stores a variety of values that describe that phase. Those values include the following:

WAVE selects which wave shape should be output by the waveform generator. In this example, WAVE is three bits, permitting the selection of eight wave shapes.

RPT sets how many times the phase should be repeated before moving on to the next phase. The phase is generated (RPT+1) times, hence RPT=0 causes the phase to be generated once, and RPT=15 causes it to be generated 16 times. In this example, RPT is four bits, permitting from 1 to 16 repetitions of the phase.

DELAY controls the duration of the delay between the end of the current phase to the start of the next phase, as will be described below. In this example, DELAY is 16 bits and the delay is (DELAY+1) microseconds long. Hence, this example supports delays of 1 µs to 65536 µs but other delays could be supported, as desired.

SYNC controls the behavior of the SYNC control signal, as will be described below. In this example, SYNC is one bit.

PAUSE controls whether the sequencer state machine should pause and wait for a rising edge on the RUN input, as described below. In this example, PAUSE is one bit.

AMP1 through AMPN contain the amplitude and polarity for channels 1 through N for a system containing N channels. In this example implementation, the amplitude values use sign-and-magnitude notation, with one sign bit and a ten bit magnitude. Thus, the amplitudes can represent values from −1023 to +1023. Numerous other representations for signed numbers could be equivalently used, including 1's complement or sign-and- magnitude. An amplitude of zero is permitted and indicates that the corresponding channel should emit no output during that phase. In this example, there are 26 channels, with 24 channels being electrically coupled to distal electrodes outside the IPG and with two channels being electrically coupled to the IPG's metallic enclosure.

Additional registers may also be included in the phase registers, as may be desired to control the behavior of the Waveform Generator, Amplitude Multipliers, or other parts of the Stimulation ASIC during that phase.

Structure of the SEQ Registers

Figure 19:
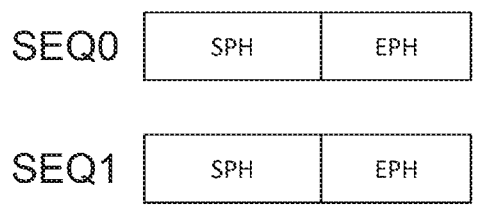
FIG. 19 is a diagram showing SEQ0 and SEQ1 registers of an example embodiment of the sequencer.

FIG. 19 shows the structure of the SEQ0 and SEQ1 register sets of this example embodiment. Both SEQ0 and SEQ1 hold two values, called SPH and EPH. SPH holds the starting phase number for the pulse train, and EPH holds the ending phase for the pulse train. The number of bits in SPH and EPH must be chosen to represent the range of 1 to m phase registers. In the example implementation, SPH and EPH are each five bits, and the range of valid values that may be stored in each ranges from 1 to 24 since this example allows up to 24 phases maximum in a pulse train.

Either of the SEQ registers (SEQ0 or SEQ1) may be used to control the sequencer state machine. The SEL control line, which is an output from the microcontroller and an input to the sequencer, selects between the two sets of SEQ registers. When SEL=0, SEQ0 is used to provide the start and end phases for the pulse train, and when SEL=1, SEQ1 is used to provide the start and end phases for the pulse train. As discussed above, this example implementation has two sets of SEQ registers. A larger number of SEQ registers could be provided if the SEL control signal was increased into more than two possible states.

Operation of the Sequencer

As described herein, the sequencer is basically a state machine implemented in digital logic within the Stimulation ASIC. It operates synchronously under the control of a periodic clock signal. In these example implementations, the clock signal runs at a frequency of 1 MHz, but other clock frequencies could be utilized, as desired. For example, to conserve power, it may be beneficial to run the clock signal at a much lower frequency for some applications.

Figure 20:
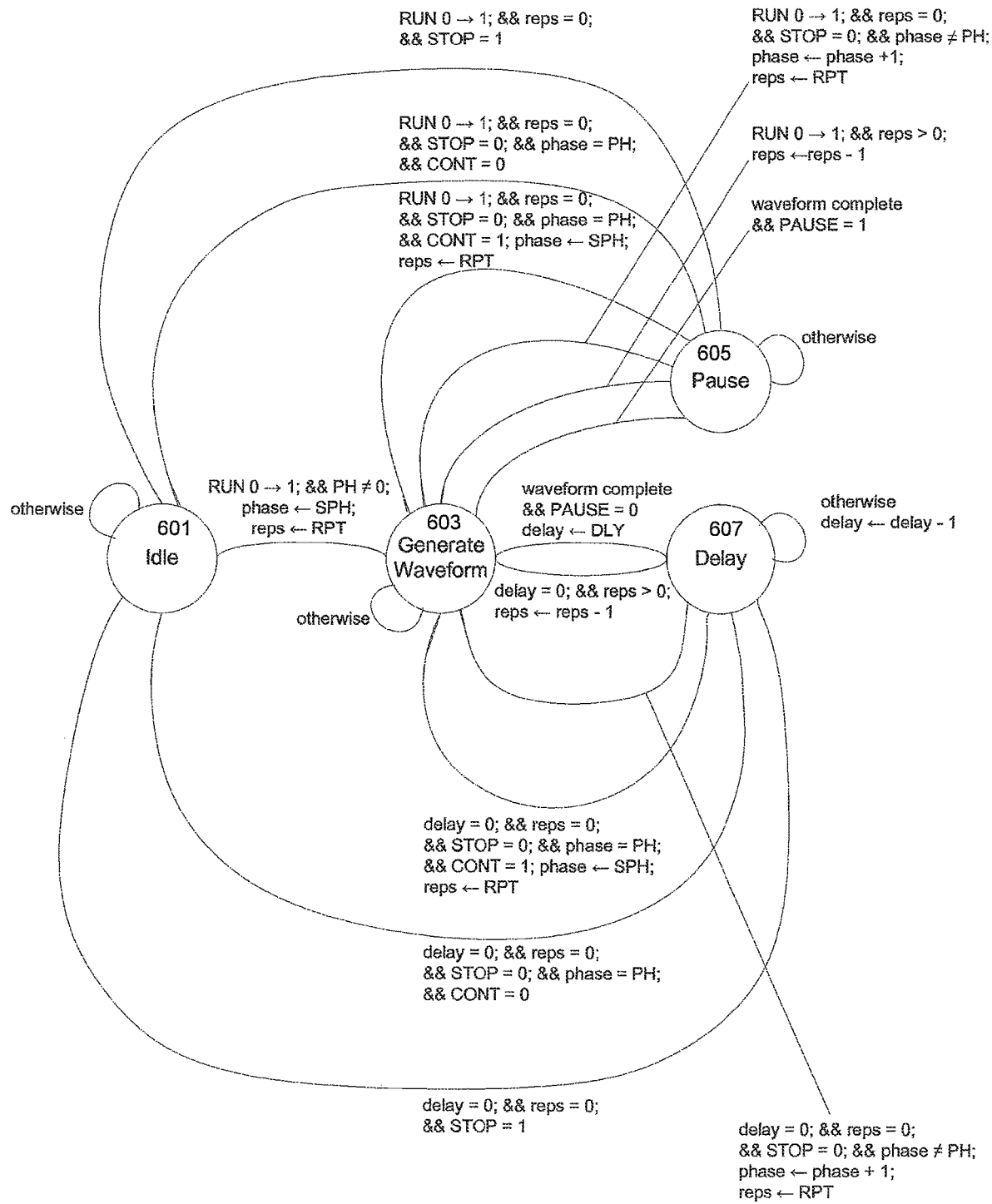
FIG. 20 is a more comprehensive state diagram a more detailed example embodiment of the sequencer.

A more comprehensive state diagram for one of the more complicated example embodiments of the sequencer is shown in FIG. 20. The sequencer starts in the Idle state 601 and remains in Idle as long as the RUN input is 0. When RUN transitions from 0 to 1, the sequencer latches the value of SPH from the SEQ register selected by the current value of the SEL input. It loads an internal register named "phase" with the value of SPH from the SEQ0 or SEQ1 register depending on the state of SEL. It also loads an internal register named "reps" with the value of RPT from the phase register bank indicated by SPH, which is the starting phase of the pulse train. The sequencer then enters the Generate Waveform state 603.

In the Generate Waveform state 603, the sequencer causes the Waveform Generator to generate the appropriate waveshape for the phase. The Waveform Generator uses the information in the phase register bank that is selected by the "phase" variable and in the other Waveform Generator memory and registers to generate the stimulation output with the amplitude and polarity on each of its output channels, as specified by that Phase Register bank. The sequencer remains in the Generate Waveform state 603 until waveshape generation is complete for that particular phase. When waveshape generation is complete, if the phase register bank's PAUSE bit is set, the sequencer enters the Pause state 605. Otherwise, it enters the Delay state 607.

In the Pause state 605, the sequencer waits for the RUN input to transition from 0 to 1. As long as RUN is stable at 0 or 1, the sequencer remains in the Pause state 605. Once RUN transitions from 0 to 1, the sequencer will enter the Idle state 601 if the STOP input is 1 and there are no more repetitions for the phase. It will also enter the Idle state 601 if the phase is the last phase of the pulse train (phase=EPH) and the CONT input is 0. The sequencer will enter the Generate Waveform state 603 if there are additional repetitions of the phase to produce (reps>0), in which case it will also decrement reps. If there are no more repetitions of the phase (reps=0), but the pulse train has not reached its end phase, the sequencer will increment its internal "phase" register, set its "reps" register to the value of RPT from the phase register bank selected by the new value of "phase", and enter the Generate Waveform state 603. Finally, if the CONT input=1, there are no more repetitions of the phase to perform, and the last phase of the pulse train has been reached, the sequencer will enter the Generate Waveform state 603 with the "phase" and "reps" registers set as they were during the initial transition out of the Idle state 601.

The Delay state 607 performs analogously to the Pause state 605, except that on entering the Delay state 607, the sequencer loads the internal "delay" register with the value DLY from the phase register bank selected by the "phase" register. With each clock cycle that the sequencer is in the Delay state 607, it decrements "delay". The sequencer leaves the Delay state 607 and enters the Idle or Generate Waveform states 601,603, respectively, in a manner identical to leaving the Pause state 605, except that instead of requiring a transition of 0 to 1 on the RUN input to exit Pause, it requires that the internal "delay" register to have decremented to 0.

The PROG handshaking line is an output from the sequencer that indicates whether the sequencer is in the Idle state 601 or any of the other states. In this example implementation, it is 0 if the sequencer is in the Idle state 601 and 1 otherwise.

This example comprehensive sequencer state machine can be applied to generate stimulation in a number of useful ways, as described below:

First, the CONT input allows the sequencer to execute a pulse train either once (called "single-shot" operation) or continuously, as selected by the microcontroller. With CONT=0, the program will run once when the microcontroller sets the RUN input from 0 to 1. In this example implementation, the RUN signal is controlled by the microcontroller's Timing Logic. Hence, the microcontroller Timing Logic can directly set the frequency of repetition of the pulse train by setting RUN from 0 to 1 at appropriate times. This mode gives the microcontroller maximum control over the repetition rate of the pulse train. However, it can be more power-efficient to put the microcontroller and its Timing Logic into a low-power sleep mode during stimulation. Also, for very high frequency stimulation, the Timing Logic may not be able to keep up with the pulse train's desired repetition rate without consuming too many microcontroller resources, leaving the microcontroller unable to perform other needed tasks. In either case, the pulse train may be set up so that its inherent cycle time is the same as the desired repetition rate by programming one or more delays in the pulse train accordingly. Then, the microcontroller can start the pulse train running with a transition from 0 to 1 on the RUN signal while holding the CONT signal at 1 for as long as the pulse train should continue to run. As can be seen from the state diagram, the sequencer will repeat the pulse train over and over, requiring no intervention from the microcontroller for continuous stimulation. The microcontroller may then attend to other tasks or may put itself into a low-power sleep mode. The microcontroller will not need to communicate with the Stimulation ASIC again until the stimulation parameters need to change or there is a need to end the stimulation.

Second, the PROG output permits the microcontroller to synchronize with the Stimulation ASIC. The clocks controlling the sequencer and the microcontroller are not necessarily synchronized. This lack of synchronization causes some variability in the time delay between the rising edge of RUN and the start of the first phase in the pulse train. The PROG output changes from 0 to 1 when the sequencer leaves the Idle state. The microcontroller can monitor PROG for this transition to determine exactly when the pulse train begins. Further, PROG changes from 1 to 0 when the sequencer enters the Idle state. The microcontroller can monitor PROG for this transition to determine when the pulse train has ended.

Third, the SYNC output synchronization with the microcontroller. The microcontroller may require information on when a particular phase, or particular phases, are performed. The SYNC bit may be programmed to one value for all phases that are not of interest and to another value for those that are of interest. The microcontroller can then monitor the SYNC control line to determine when those phases are being executed. Similarly, if the SYNC bits of successive phases are programmed to alternating 1 and 0, each rising and falling edge of the SYNC control line will represent the transition from one phase to the next. The microcontroller can monitor those edges and track the progression of the pulse train through each phase.

Fourth, the PAUSE feature permits additional synchronization with the microcontroller. If PAUSE=1 for a given phase, the waveform for that phase is followed by an interval with no output. The duration of that interval is controlled by the microcontroller, and ends when microcontroller sets the RUN signal from 0 to 1. Thus, if the delay between two phases in a pulse train is desired to be longer than the maximum delay available in the DELAY register, that can be easily accommodated by the Stimulation ASIC using PAUSE. Also, if the delay needs to be variable, the microcontroller can use its firmware and Timing Logic to directly control the delay using PAUSE. This could be used, for example, to let the microcontroller directly control the start time of each phase within a pulse train.

Fifth, the STOP handshaking line allows the microcontroller to terminate the pulse train without waiting for the pulse train to complete (such as due to detection of a system fault by the microcontroller). As can be seen in the state diagram of FIG. 20, when STOP is 1, all repetitions of the current phase are executed, then the sequencer enters the Idle state without performing the remaining phases in the pulse train. The microcontroller can monitor the PROG control line to determine when the pulse train has ended and the sequencer is in the Idle state 601. If necessary, the microcontroller can use its Timing Logic or information obtained from the SYNC control line to determine what phase was being performed when STOP was set to 1.

The interaction of STOP and CONT is worth noting. It can be seen in the state diagram in FIG. 20 that STOP takes precedence over CONT, which provides two ways to end a continuously-executing pulse train (CONT=1). First, at any time, CONT may be set to 0. The sequencer will then complete the pulse train before entering the Idle state 601. Alternately, STOP may be set to 1, with or without setting CONT to 0, in which case the sequencer will enter the Idle state 601 immediately after completing all repetitions of current phase. Which of these modes is preferable can depend on the pulse train being generated and the reason for ending it.

The Delay state of the sequencer, with the DLY field of the phase registers, permits the generation of a delay between pulses. The final delay at the end of the pulse train can be programmed in such a way that it determines the pulse train's repetition rate in continuous operation (CONT=1). In this implementation, the delay between each phase in a pulse train can be as low as 1 μs or as high as 65,536 μs. If a longer delay is required or otherwise desired, such as when generating low-frequency stimulation in continuous mode, it is possible to add extra phases to the pulse train with all amplitudes set to 0 and to repeat phases using the RPT field in the phase register to create longer delays.

The RPT field of the phase registers, in conjunction with the sequencer state machine, permits the efficient generation of burst or n-let stimulation by repeating one or more phases in a pulse train as many times as desired.

Microcontroller Interaction with the Sequencer

Figure 21:
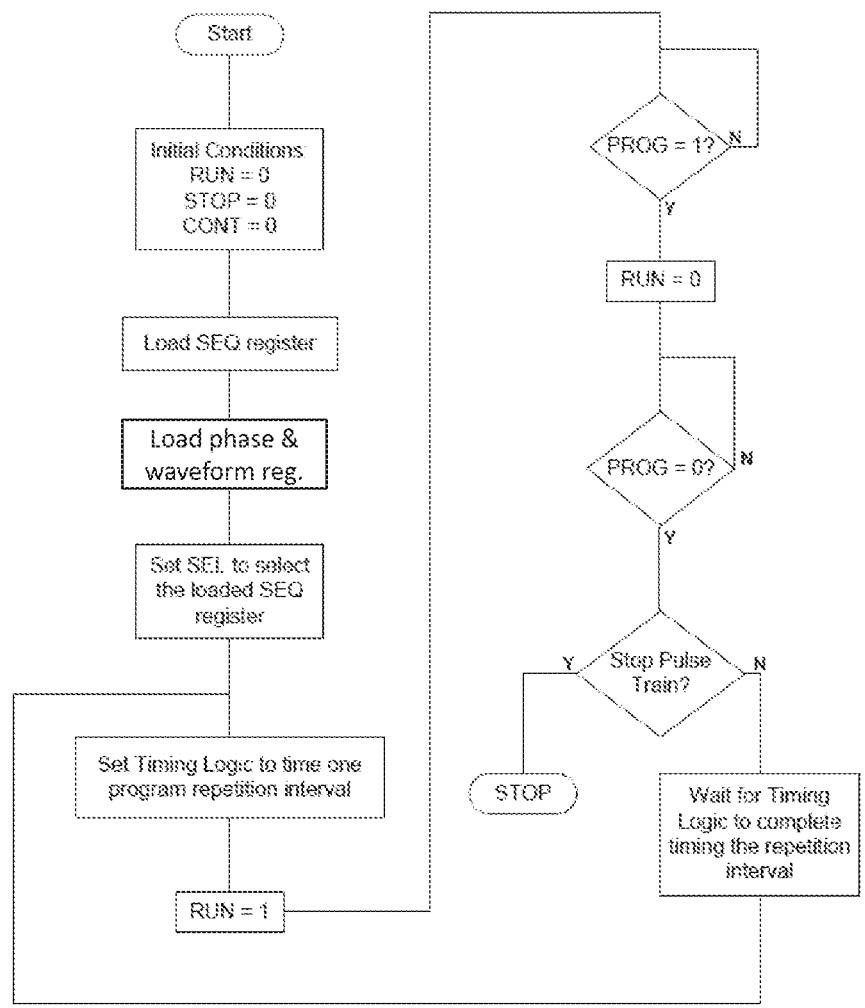
FIG. 21 is a flow chart describing an example operation of an example sequencer for generating a repeating pulse train.

FIG. 21 is a flow chart describing an example operation of the firmware when generating a repeating pulse train with the Stimulation ASIC, with timing of the repetition rate provided by the Timing Logic on the microcontroller. As can be seen in the figure, operation starts with the initial conditions that the RUN, STOP, and CONT outputs from the microcontroller are all set to 0. In the "Load Program" step, the microcontroller then uses a serial interface on the Stimulation ASIC to load one SEQ register and whatever set of phase registers, waveform generator memory, and waveform generator registers are needed for the desired stimulation output. Note that the SEQ register could be loaded ("load SEQ Register") before (as shown) or after loading all other registers without altering the effect of the algorithm. Once all of the data is loaded, the microcontroller sets its SEL output to select the SEQ register loaded earlier, then the microcontroller sets its RUN output from 0 to 1. After waiting for the sequencer to set PROG to 1 to acknowledge the start of the pulse train, the microcontroller sets RUN to 0 so that it will be ready for the next iteration of the pulse train. It then waits for PROG to return to 0. Once PROG is 0, the microcontroller knows the sequencer has completed the final phase in the pulse train, and a decision must be made based on the firmware's programming whether to repeat the pulse train. If the firmware instructions tell the microcontroller to repeat the pulse train, the microcontroller uses its timing logic to wait until it is time to start the next repetition of the pulse train, at which point the microcontroller loops back to initiate another run of the program of the sequencer by setting RUN from 0 to 1. The process continues until the firmware tells the microcontroller to stop stimulation.

Figure 22:
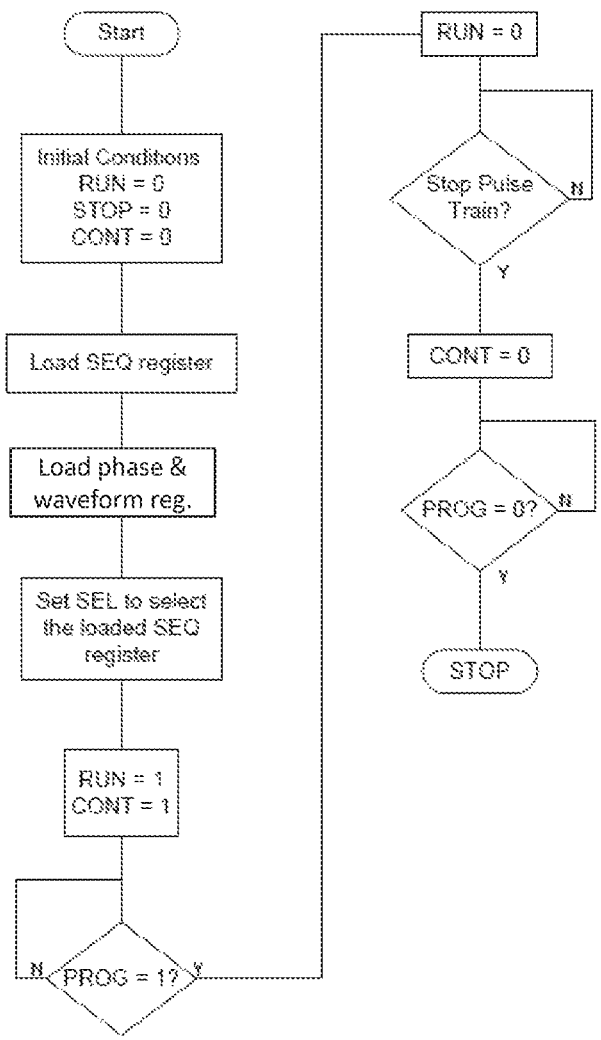
FIG. 22 is a flow chart showing an example operation of an example sequencer using a continuous operation feature.

FIG. 22 is a flow chart showing the typical operation of the example firmware when using the continuous operation feature of the example sequencer. As in FIG. 21, the microcontroller starts with the initial state of RUN=CONT=STOP=0. The microcontroller then loads the SEQ register, phase registers, waveform generator memory, and waveform generator registers that are needed for the desired stimulation output, and sets SEL to select the SEQ register. The pulse train must be configured so that its cycle time is equal to the desired repetition rate. The microcontroller then sets RUN from 0 to 1, as before, but also sets CONT to 1 to enable continuous operation in the sequencer. It waits for PROG to go to 1 as the sequencer starts executing the pulse train, then sets RUN to 0 in preparation for future initial conditions. The microcontroller then waits until its firmware instructions indicate that stimulation should stop. Once the firmware instructions indicate that it is time to stop stimulation, the microcontroller sets CONT to 0, then waits for PROG to go to 0 to indicate that the sequencer has executed the final phase of the pulse train.

Figure 23:
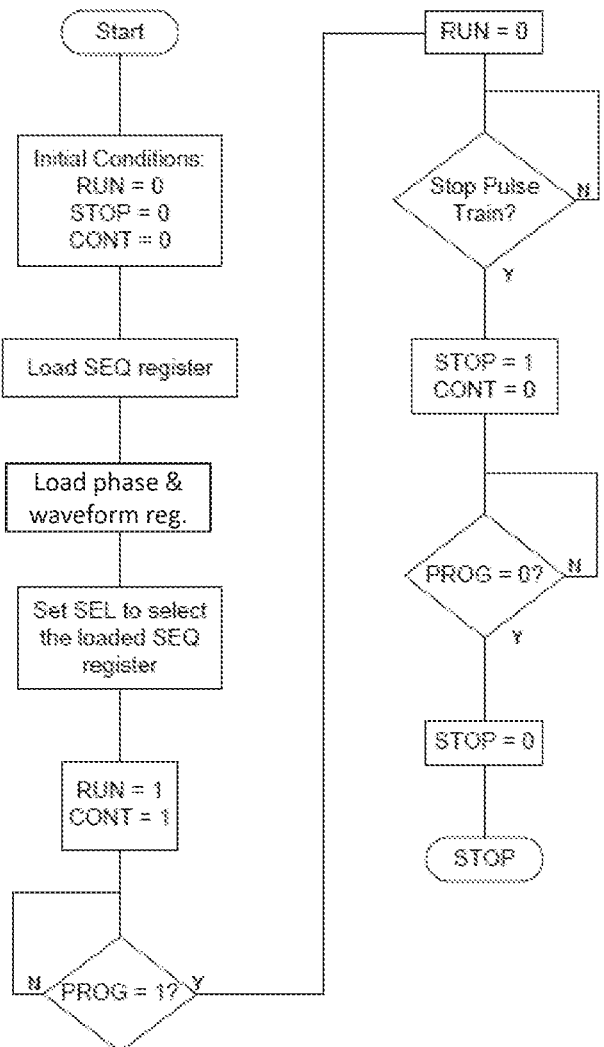
FIG. 23 is a flow chart showing another example operation of the an example sequencer using another continuous operation feature.

FIG. 23 is a flow chart showing the operation of the example firmware when using the continuous operation feature of the example sequencer, but ending the pulse train in the middle via the STOP control signal. The initial steps up to determining whether to stop the pulse train are identical as described above. However, after the firmware instructions indicate that it is time to stop the pulse train, the microcontroller sets STOP to 1 and CONT to 0. The sequencer, on detecting that STOP is set to 1, ends the pulse train after the current phase, instead of completing the pulse train as happens in FIG. 22. The microcontroller waits for PROG to go to 0 to indicate that the pulse train has terminated. Once PROG has gone to 0, the microcontroller sets STOP to 0 in preparation for the initial conditions of a future procedure. Note that CONT could be set to 0 at any time after STOP is set to 1. Performing both operations at substantially the same time, as shown in FIG. 23, is typical.

Figure 24A:
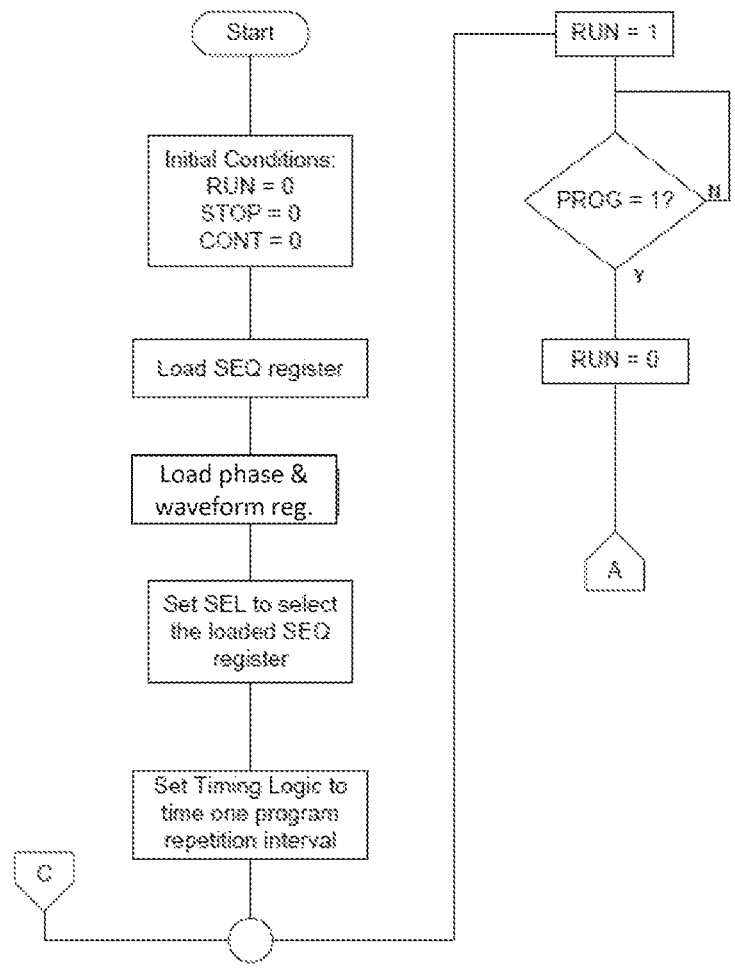
FIGS. 24a, 24b, and 24c together provide a flow chart of an example operation of an example sequencer using a PAUSE feature.
Figure 24B:
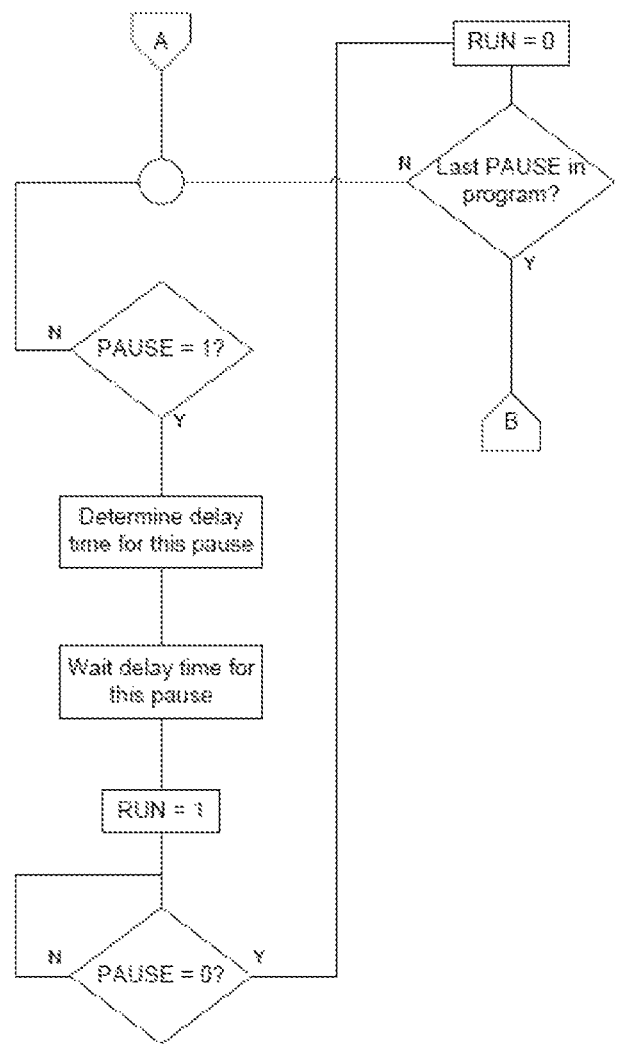
Figure 24C:
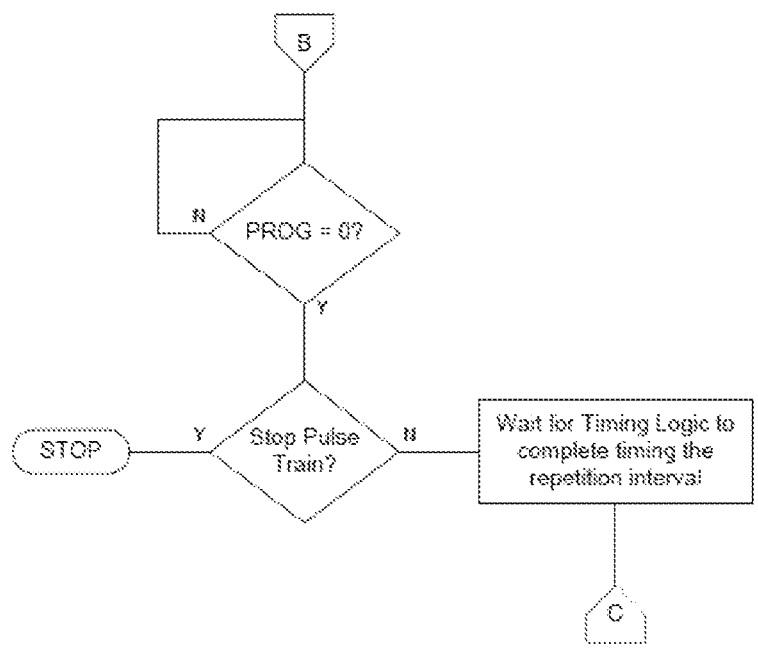

FIGS. 24a, 24b, and 24c together provide a flow chart of an example operation of the example firmware when using the PAUSE feature of the example sequencer. To use this mode of operation, the firmware should keep a list of each pause in the pulse train and the delay that the Timing Logic must produce for each pause. Similarly as in previous examples, operation starts with the initial conditions that the RUN, STOP, and CONT outputs from the microcontroller are all set to 0. The microcontroller then uses the serial interface on the Stimulation ASIC to load one SEQ register and whatever set of phase registers, waveform generator memory, and waveform generator registers are necessary for generating the desired pulse train. At least one set of phase registers should be programmed so that the PAUSE bit is set to 1. Note that the SEQ register could be loaded before or after the other registers without changing the function of this process.

Once all of the necessary registers are loaded, the microcontroller sets the SEL control signal to select the SEQ register loaded earlier and configures the Timing Logic to a specific time interval. The microcontroller then sets its RUN output from 0 to 1. After waiting for the sequencer to set PROG to 1 to acknowledge the start of the pulse train, the microcontroller sets RUN to 0 so that it will be ready for the first pause. The microcontroller then waits for the PAUSE control signal to be set to 1. The microcontroller determines the correct delay time for the pause, uses the Timing Logic to wait the delay time, then sets RUN from 0 to 1 to end the pause and cause the sequencer to resume the next phase in the pulse train. Once the sequencer sets PAUSE to 0, the microcontroller sets RUN back to 0 in preparation for the next pause. The microcontroller checks if this is the last pause in the pulse train. If it is not the last pause, the microcontroller loops back to the previous steps, starting with waiting for PAUSE to be set to 1 by the sequencer. If this is the last pause in the pulse train, the microcontroller waits for PROG to be set to 0, indicating that the final phase in the pulse train has been executed. The microcontroller then uses its firmware programming to determine if stimulation should stop or if the pulse train should be repeated. If the pulse train should continue, the microcontroller uses its Timing Logic to wait until the repetition interval is complete, then loops back to run the pulse train again, starting by setting RUN from 0 to 1.

Figure 25A:
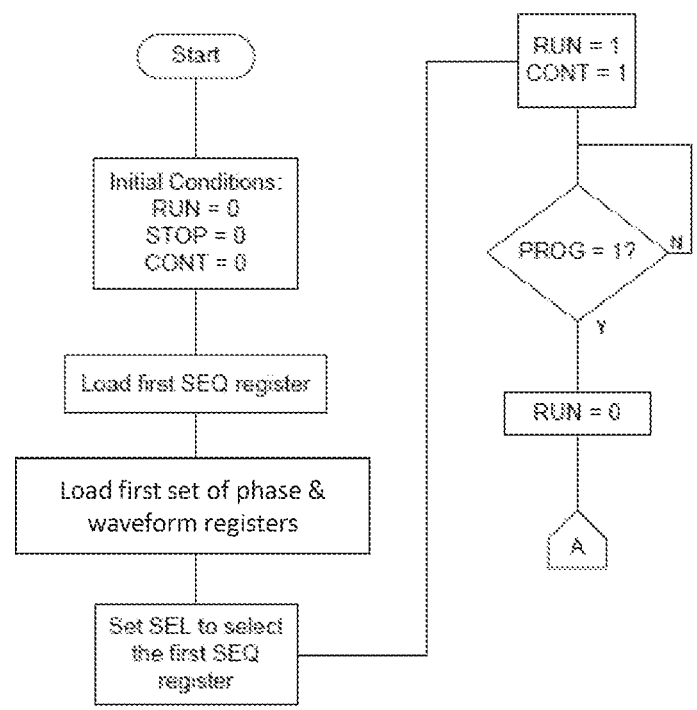
FIGS. 25a and 25b together provide a flow chart of an example operation of an example sequencer using double-buffering to update stimulation parameters during continuous operation.
Figure 25B:
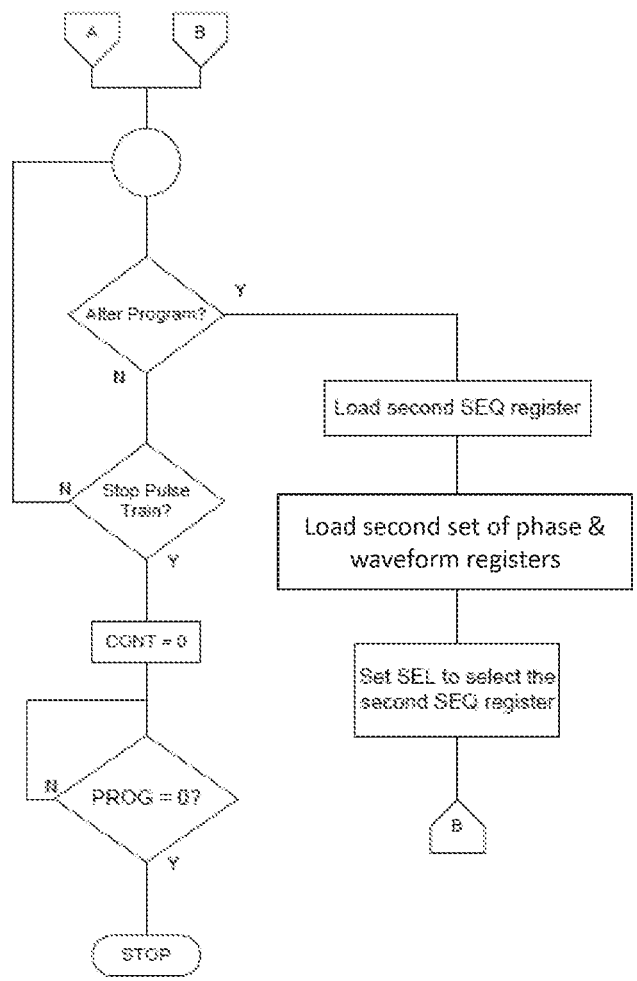

FIGS. 25a and 25b together provide a flow chart showing the operation of the example firmware when using double-buffering to update stimulation parameters during continuous operation. The microcontroller starts with the initial state of RUN=CONT=STOP=0. The microcontroller then loads a first SEQ register, loads a first set of data into a first subset of the registers and memory, and sets SEL to select the first SEQ register. The pulse train must be configured so that its cycle time is equal to the desired repetition rate. The microcontroller then sets RUN from 0 to 1, as before, but also sets CONT to 1 to enable continuous operation in the sequencer. The microcontroller waits for PROG to go to 1 as the sequencer starts the pulse train, then sets RUN to 0 in preparation for future initial conditions.

Now that the example sequencer is running the pulse train autonomously, the microcontroller waits for (or is otherwise utilized until) one of two events: Either the firmware instructions indicate that the stimulation parameters should be altered, or the pulse train should be stopped. If the pulse train should stop, the microcontroller sets CONT to 0, then waits for PROG to go to 0 to indicate that the sequencer has executed the final phase of the pulse train. However, if the stimulation parameters should be altered, the microcontroller loads a second SEQ register and loads the new stimulation parameters into a second subset of the registers and memory. The new stimulation parameters might generate a similar pulse train as the first pulse train, except one or more parameters could be different. It is also possible that the new pulse train could be entirely different from the first. Once the new stimulation parameters are loaded into the second subset of the registers and memory, the microcontroller sets the SEL line to select the second SEQ register. As can be seen in the sequencer state diagram in FIG. 20, the sequencer will complete the execution of all phases of the first pulse train, then will begin executing the second pulse train as soon as the first pulse train is complete. Thus, by this procedure, the microcontroller can cause the example sequencer to alter the stimulation output from one pulse train to another with no interruption of the stimulation output and with no glitches or incomplete pulse train execution.

The double-buffering technique can also be applied when the repetition rate is controlled by the microcontroller's Timing Logic. The steps needed are analogous to those of FIGS. 25a-25b, though the loading of the second pulse train is preferably done while the microcontroller is waiting for a change of state on a control line or waiting for the Timing Logic to time an interval. In order to maintain the desired repetition rate of the pulse train, it may be desirable to load the second pulse train in several small pieces.

For the microcontroller procedures described above, during times where the microcontroller is waiting for a signal from the sequencer or for some amount of time to elapse, it is beneficial for the microcontroller to perform other tasks and/or enter a low-power sleep mode while it waits.

The procedures described above and shown in the figures are examples to explain the interface between the microcontroller and the example sequencer. Numerous variations are possible. Higher performance in the system may be obtained by performing the operations described in response to various interrupts provided by the microcontroller and Timing Logic. The various steps may also be divided between tasks managed by a multitasking operating system running on the microcontroller. Multiple features may be combined. For example, double-buffering can be combined with PAUSE handling or with running two pulse trains at different rates. Other modifications are clearly also available.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

The invention claimed is:

1. A pulse generator, comprising:
a stimulation circuit configured to generate a plurality of different stimulation signals;
a first output channel configured to output a first stimulation signal of the plurality of different stimulation signals to a patient, wherein the first stimulation signal has a first waveform shape;
a second output channel configured to output a second stimulation signal of the plurality of different stimulation signals to the patient, wherein the second stimulation signal has a second waveform shape different from the first waveform shape, and wherein the first stimulation signal and the second stimulation signal are outputted simultaneously;
a third output channel configured to output a third stimulation signal of the plurality of different stimulation signals to the patient, wherein the third stimulation signal has a third waveform shape that is different from the first waveform shape and the second waveform shape; and
a fourth output channel configured to output a fourth stimulation signal of the plurality of different stimulation signals to the patient, wherein the fourth stimulation signal has a fourth waveform shape different from the first waveform shape, the second waveform shape, and the third waveform shape, and wherein the first stimulation signal, the second stimulation signal, the third stimulation signal, and the fourth stimulation signal are outputted simultaneously;
wherein:
the first stimulation signal, the second stimulation signal, the third stimulation signal, and the fourth stimulation signal each comprise a plurality of phases;
at a first phase of the plurality of phases, the first stimulation signal and the second stimulation signal are active, while the third stimulation signal and the fourth stimulation signal are off;
at a second phase of the plurality of phases different from the first phase, the first stimulation signal and the second stimulation signal are off, while the third stimulation signal and the fourth stimulation signal are active;
at a third phase of the plurality of phases that occurs after the first phase and the second phase, charge balancing occurs for a first subset of: the first stimulation signal, the second stimulation signal, the third stimulation signal, and the fourth stimulation signal; and
at a fourth phase of the plurality of phases that occurs after the third phase, charge balancing occurs for a second subset of: the first stimulation signal, the second stimulation signal, the third stimulation signal, and the fourth stimulation signal, wherein the first subset and the second subset are mutually exclusive from each other.

2. The pulse generator of claim 1, wherein the second waveform shape is an inverse of the first waveform shape.

3. The pulse generator of claim 1, wherein the first output channel and the third output channel are configured to output the first stimulation signal and the third stimulation signal to different types of nerve fibers.

4. The pulse generator of claim 1, wherein:
the first stimulation signal and the second stimulation signal have a first type of waveform shape during the first phase;
the third stimulation signal and the fourth stimulation signal have a second type of waveform shape during the second phase; and
the first type of waveform shape is different from the second type of waveform shape.

5. The pulse generator of claim 1, wherein:
the first subset includes the first stimulation signal and the second stimulation signal; and
the second subset includes the third stimulation signal and the fourth stimulation signal.

6. The pulse generator of claim 1, wherein:
the first subset includes the third stimulation signal and the fourth stimulation signal; and
the second subset includes the first stimulation signal and the second stimulation signal.

7. The pulse generator of claim 1, wherein:
at the third phase, the second subset of the first stimulation signal, the second stimulation signal, the third stimulation signal, and the fourth stimulation signal are turned off; and
at the fourth phase, the first subset of the first stimulation signal, the second stimulation signal, the third stimulation signal, and the fourth stimulation signal are turned off.

8. A method, comprising:
generating, via a stimulation circuit of a pulse generator, a plurality of different stimulation signals;
applying, via a first output channel, a first stimulation signal of the plurality of different stimulation signals to a patient, wherein the first stimulation signal has a first waveform shape;
applying, via a second output channel, a second stimulation signal of the plurality of different stimulation signals to the patient, wherein the second stimulation signal has a second waveform shape different from the first waveform shape, and wherein the first stimulation signal and the second stimulation signal are applied to the patient simultaneously;
applying, via a third output channel, a third stimulation signal of the plurality of different stimulation signals to the patient, wherein the third stimulation signal has a third waveform shape that is different from the first waveform shape and the second waveform shape; and
applying, via a fourth output channel, a fourth stimulation signal of the plurality of different stimulation signals to the patient, wherein the fourth stimulation signal has a fourth waveform shape different from the first waveform shape, the second waveform shape, and the third waveform shape, and wherein the first stimulation signal, the second stimulation signal, the third stimulation signal, and the fourth stimulation signal are outputted simultaneously;

wherein:

the first stimulation signal, the second stimulation signal, the third stimulation signal, and the fourth stimulation signal each comprise a plurality of phases;

at a first phase of the plurality of phases, the first stimulation signal and the second stimulation signal are active, while the third stimulation signal and the fourth stimulation signal are off;

at a second phase of the plurality of phases different from the first phase, the first stimulation signal and the second stimulation signal are off, while the third stimulation signal and the fourth stimulation signal are active;

at a third phase of the plurality of phases that occurs after the first phase and the second phase, charge balancing occurs for a first subset of: the first stimulation signal, the second stimulation signal, the third stimulation signal, and the fourth stimulation signal; and at a fourth phase of the plurality of phases that occurs after the third phase, charge balancing occurs for a second subset of: the first stimulation signal, the second stimulation signal, the third stimulation signal, and the fourth stimulation signal, wherein the first subset and the second subset are mutually exclusive from each other.

9. The method of claim 8, wherein the second waveform shape is an inverse of the first waveform shape.

10. The method of claim 8, wherein:
the first stimulation signal and the second stimulation signal are applied to polarize nerves in a first tissue area; and
the third stimulation signal and the fourth stimulation signal are applied to stimulate nerves in a second tissue area after the nerves in the first tissue area are polarized in response to the first stimulation signal.

11. The method of claim 8, wherein:
the first stimulation signal and the second stimulation signal have a first type of waveform shape during the first phase;
the third stimulation signal and the fourth stimulation signal have a second type of waveform shape during the second phase; and
the first type of waveform shape is different from the second type of waveform shape.

12. The method of claim 8, wherein:
the first subset includes the first stimulation signal and the second stimulation signal; and
the second subset includes the third stimulation signal and the fourth stimulation signal.

13. The method of claim 8, wherein:
the first subset includes the third stimulation signal and the fourth stimulation signal; and
the second subset includes the first stimulation signal and the second stimulation signal.

14. The method of claim 8, wherein:
at the third phase, the second subset of the first stimulation signal, the second stimulation signal, the third stimulation signal, and the fourth stimulation signal are turned off; and
at the fourth phase, the first subset of the first stimulation signal, the second stimulation signal, the third stimulation signal, and the fourth stimulation signal are turned off.

15. A medical system, comprising:
an implantable lead having a plurality of electrodes; and
an implantable pulse generator having a stimulation circuit configured to generate a plurality of different stimulation signals and a plurality of output channels that can each output a stimulation signal to a patient via a respective one of the electrodes on the implantable lead;

wherein:

the stimulation circuit causes a first output channel of the plurality of output channels to output a first stimulation signal of the plurality of different stimulation signals, the first stimulation signal having a first waveform shape;

the stimulation circuit causes a second output channel of the plurality of output channels to output a second stimulation signal of the plurality of different stimulation signals, the second stimulation signal having a second waveform shape that is different from the first waveform shape, the first stimulation signal and the second stimulation signal being outputted simultaneously;

the stimulation circuit causes a third output channel of the plurality of output channels to output a third stimulation signal of the plurality of different stimulation signals, wherein the third stimulation signal has a third waveform shape that is different from the first waveform shape and the second waveform shape;

the stimulation circuit causes a fourth output channel of the plurality of output channels to output a fourth stimulation signal of the plurality of different stimulation signals, wherein the fourth stimulation signal has a fourth waveform shape different from the first waveform shape, the second waveform shape, and the third waveform shape, and wherein the first stimulation signal, the second stimulation signal, the third stimulation signal, and the fourth stimulation signal are outputted simultaneously;

the first stimulation signal, the second stimulation signal, the third stimulation signal, and the fourth stimulation signal each comprise a plurality of phases;

at a first phase of the plurality of phases, the first stimulation signal and the second stimulation signal are active, while the third stimulation signal and the fourth stimulation signal are off;

at a second phase of the plurality of phases different from the first phase, the first stimulation signal and the second stimulation signal are off, while the third stimulation signal and the fourth stimulation signal are active;

at a third phase of the plurality of phases that occurs after the first phase and the second phase, charge balancing occurs for a first subset of: the first stimulation signal, the second stimulation signal, the third stimulation signal, and the fourth stimulation signal;

at a fourth phase of the plurality of phases that occurs after the third phase, charge balancing occurs for a second subset of: the first stimulation signal, the second stimulation signal, the third stimulation signal, and the fourth stimulation signal, wherein the second subset is different from the first subset; and the second waveform shape is an inverse of the first waveform shape for two or more phases of the plurality of phases.

16. The medical system of claim 15, wherein the second waveform shape is the inverse of the first waveform shape for the first phase, the second phase, the third phase, and the fourth phase.

17. The medical system of claim 15, wherein:
the first stimulation signal and the second stimulation signal are applied, via a first set of electrodes, to polarize nerves in a first tissue area; and
the third stimulation signal and the fourth stimulation signal are applied, via a second set of electrodes, to stimulate nerves in a second tissue area different from the first tissue area.

18. The medical system of claim 15, wherein:
the first stimulation signal and the second stimulation signal have a first type of waveform shape during the first phase;
the third stimulation signal and the fourth stimulation signal have a second type of waveform shape during the second phase; and
the first type of waveform shape is different from the second type of waveform shape.

19. The medical system of claim 15, wherein:
the first subset includes the first stimulation signal and the second stimulation signal;
the second subset includes the third stimulation signal and the fourth stimulation signal;
at the third phase, the third stimulation signal and the fourth stimulation signal are turned off; and
at the fourth phase, the first stimulation signal and the second stimulation signal are turned off.

20. The method of claim 8, wherein:
the first subset includes the third stimulation signal and the fourth stimulation signal;
the second subset includes the first stimulation signal and the second stimulation signal;
at the third phase, the first stimulation signal and the second stimulation signal are turned off; and
at the fourth phase, the third stimulation signal and the fourth stimulation signal are turned off.

* * * * *